United States Patent
Su'etsugu et al.

(10) Patent No.: US 12,157,915 B2
(45) Date of Patent: Dec. 3, 2024

(54) METHOD OF AMPLIFYING CIRCULAR DNA

(71) Applicant: MODERNA ENZYMATICS CO., LTD., Tokyo (JP)

(72) Inventors: Masayuki Su'etsugu, Tokyo (JP); Hiroko Tsujimoto, Tokyo (JP); Takeshi Shinohara, Tokyo (JP)

(73) Assignee: Moderna Enzymatics Co., Ltd., Tokyo (JP)

( * ) Notice: Subject to any disclaimer, the term of this patent is extended or adjusted under 35 U.S.C. 154(b) by 1496 days.

(21) Appl. No.: 16/302,485

(22) PCT Filed: May 17, 2017

(86) PCT No.: PCT/JP2017/018472
§ 371 (c)(1),
(2) Date: Nov. 16, 2018

(87) PCT Pub. No.: WO2017/199991
PCT Pub. Date: Nov. 23, 2017

(65) Prior Publication Data
US 2019/0276883 A1     Sep. 12, 2019

(30) Foreign Application Priority Data
May 17, 2016 (JP) ................. 2016-099157

(51) Int. Cl.
| | | |
|---|---|---|
| C12P 19/34 | (2006.01) | |
| C12N 15/09 | (2006.01) | |
| C12Q 1/6844 | (2018.01) | |
| C12Q 1/6855 | (2018.01) | |
| C12Q 1/686 | (2018.01) | |

(52) U.S. Cl.
CPC ........... *C12Q 1/6855* (2013.01); *C12N 15/09* (2013.01); *C12P 19/34* (2013.01); *C12Q 1/6844* (2013.01); *C12Q 1/686* (2013.01); *C12Q 2521/101* (2013.01); *C12Q 2521/319* (2013.01); *C12Q 2521/327* (2013.01); *C12Q 2521/501* (2013.01); *C12Q 2521/513* (2013.01); *C12Q 2521/519* (2013.01); *C12Q 2522/101* (2013.01); *C12Q 2525/307* (2013.01); *C12Q 2527/101* (2013.01); *C12Q 2527/125* (2013.01); *C12Q 2531/10* (2013.01); *C12Q 2563/159* (2013.01); *C12Y 301/04001* (2013.01); *C12Y 306/04012* (2013.01)

(58) Field of Classification Search
CPC ........... C12Q 1/6844; C12Q 2521/101; C12Q 2521/319; C12Q 2521/327; C12Q 2521/501; C12Q 2521/513; C12Q 2521/519; C12Q 2522/101; C12Q 2527/101; C12Q 2527/125
See application file for complete search history.

(56) References Cited

U.S. PATENT DOCUMENTS

| | | |
|---|---|---|
| 6,340,476 B1 | 1/2002 | Midha et al. |
| 6,506,581 B1 | 1/2003 | Fleischmann et al. |
| 10,301,672 B2 | 5/2019 | Su'etsugu et al. |
| 2010/0028862 A1 | 2/2010 | Jarvis et al. |
| 2017/0321263 A1 | 11/2017 | Su'etsugu et al. |
| 2019/0249236 A1 | 8/2019 | Su'etsugu et al. |
| 2020/0115727 A1 | 4/2020 | Su'etsugu et al. |

FOREIGN PATENT DOCUMENTS

| | | |
|---|---|---|
| EP | 1916311 A1 | 4/2008 |
| EP | 3222717 A1 | 9/2017 |
| JP | 2005229950 A | 9/2005 |
| JP | 2008161182 A | 7/2008 |
| JP | 2012501173 A | 1/2012 |
| WO | 199523875 A1 | 9/1995 |
| WO | 200078977 A1 | 12/2000 |
| WO | 2010026099 A1 | 3/2010 |
| WO | 2016080424 A1 | 5/2016 |

OTHER PUBLICATIONS

Hiasa et al. Journal of Biological Chemistry 1994; 269: 2093-2099 (Year: 1994).*
Kelman, Z. and O'Donnell, M. DNA Polymerase III Holoenzyme: Structure and Function of a Chromosomal Replicating Machine. Annual Review of Biochemistry, 1995: 64: 171-200 (Year: 1995).*
Wowor et al. Thermodynamics of the DNA Structural Selectivity of the Pol I DNA Polymerases from *Escherichia coli* and Thermus aquaticus. Biophysical Journal 2010; 98: 3015-3024 (Year: 2010).*
Duigou et al. ssb gene duplication restores the viability of ΔholC and ΔholD *Escherichia coli* mutants. PLos Genetics 2014; 10(10): e1004719. doi:10.1371/journal.pgen.1004719. (Year: 2014).*
Slater et al. holE, the gene coding for the theta subunit of DNA polymerase III of *Escherichia coli*: characterization of a holE mutant and comparison with a dnaQ (epsilon-subunit) mutant. Journal of Bacteriology 1994; 176(3): 815-821 (Year: 1994).*
Bailey et al. (2015) "Termination of DNA Replication Forks: Breaking up is hard to do", Nucleus, 6(3): 187-196.

(Continued)

*Primary Examiner* — Angela M. Bertagna
(74) *Attorney, Agent, or Firm* — Suzannah K. Sundby, Esq.; Canady + Lortz LLP

(57) ABSTRACT

Provided is a method capable of simply and exponentially amplifying circular DNA, and particularly, long-chain circular DNA, in a cell-free system. Specifically, provided herein is a method for amplifying circular DNA which comprises mixing circular DNA having a replication origin sequence (origin of chromosome (oriC)) with a reaction solution comprising: a first enzyme group that catalyzes replication of circular DNA; a second enzyme group that catalyzes an Okazaki fragment maturation and synthesizes two sister circular DNAs constituting a catenane; a third enzyme group that catalyzes a separation of two sister circular DNAs; and also, a buffer, NTP, dNTP, a magnesium ion source, and an alkali metal ion source, to form a reaction mixture, which is then reacted.

15 Claims, 24 Drawing Sheets

(56) References Cited

OTHER PUBLICATIONS

C.Y.IP et al. (Dec. 1, 2003) "Decatenation of DNA Circles by FtsK-dependent Xer site-specific Recombination", The EMBO Journal, 22(23): 6399-6407.
Beattie et al. (Jun. 5, 2015) "A Replisome's Journey Through The Bacterial Chromosome", Frontiers in Microbiology, 6:562.
Kuzminov A. (Dec. 1999) "Recombinational Repair Of DNA Damage In *Escherichia coli* And Bacteriophage Lambda", Microbiology and Molecular Biology Reviews, 63(4):751-813.
Hiasa, H. et al. (1994). "Primase Couples Leading- and Lagging-strand DNA." The Journal of Biological Chemistry 269(8): 6058-6063.
Chao, R. et al. (2015). "Recent advances in DNA assembly technologies." FEMS Yeast Research 15:1-9.
Chen, Z. et al. (Dec. 1, 1998). "Amplification of closed circular DNA in vitro," Nucleic Acids Res 26 (23):1126-1127.
Extended European Search Report mailed on Dec. 16, 2019 for European Application No. 17799415.9, filed on May 17, 2017. 5 pages.
Extended European Search Report mailed on Mar. 27, 2018, for EP Application No. 15860324.1, 9 pages.
Funnell, B. et al. (Apr. 25, 1986). "Complete enzymatic replication of plasmids containing the origin of the *Escherichia coli* chromosome," J Biol Chem 261(12):5616-5624.
Gusev, Y. et al. (2001). "Rolling circle amplification: A new approach to increase sensitivity for immunohistochemistry and flow cytometry." American Journal of Pathology 159(1):63-69.
Hiasa, H. et al. (1994). "Topoisomerase IV can support OriC DNA replication in vitro." The Journal of Biological Chemistry 269(23):16371-16375.
Hiasa, H. et al. (1994). "Tus prevents overreplication of oriC plasmid DNA." The Journal of Biological Chemistry 269 (43):26959-26968.
Hiasa, H. et al. (1994). "Topoisomerase III, but not topoisomerase I, can support nascent chain elongation during theta-type DNA replication." The Journal of Biological Chemistry 269(51):32655-32659.
International Search Report mailed on May 29, 2018 for International Application No. PCT/JP2018/007485, filed on Feb. 28, 2018. 2 pages.
International Search Report mailed on Aug. 15, 2017 for International Application No. PCT/JP2017/018472, filed May 17, 2017. 5 pages.
International Search Report mailed on Feb. 16, 2016 for International Application No. PCT/JP2015/082356, filed Nov. 18, 2015. 2 pages.
Kaguni, J. et al. (1984). "Replication initiated at the origin (OriC) of the *E. coli* chromosome reconstituted with purified enzymes." Cell 38:183-190.
Peng, H. et al. (1993). "Decatenation activity of topoisomerase IV during oriC and pBR322 DNA replication in vitro." Proceedings of the National Academy of Sciences USA 90:8571-8575.
Su'Etsugu, M. et al. (Nov. 16, 2017). "Exponential propagation of large circular DNA by reconstitution of a chromosome-replication cycle," Nucleic Acids Res 45(20):11525-11534.
Suski, C. et al. (2008). "Resolution of converging replication forks by RecQ and topoisomerase III." Molecular Cell 30 (6):779-789.
Tsuge, K. et al. (2003). "One step assembly of multiple DNA fragments with a designed order and orientation in Bacillus subtillis plasmid." Nucleic Acids Research vol. 31, No. 21. 8 pages.
Fakruddin, M. et al. (2013). "Nucleic acid amplification: Alternative methods of polymerase chain reaction." Journal of Pharmacy and Bioallied Sciences 5(4):245-252.
Hiasa, H. et al. (Jan. 21, 1994). "Decatenating Activity of *Escherichia coli* DNA Gyrase and Topoisomerases I and III during oriC and pBR322 DNA Replication in Vitro." The Journal of Biological Chemistry 269(3):2093-2099.

\* cited by examiner oriC- Km fragment (2.3 kb)

Cyclization by
ligation of PCR
fragments
(Gibson assembly)

dnaA-dnaN fragment
(2.6 kb)

a)

b)

Condition A

Condition B miniChr: minichromosome (8-kb circular DNA)

Condition Q

Condition R 0.8 ng/μl DNA, 30°C 60min

Condition S          80 kb DNA (8 ng/μl), 30°C 120min

METHOD OF AMPLIFYING CIRCULAR DNA

TECHNICAL FIELD

The present invention relates to a method for amplifying circular DNA. More specifically, the present invention relates to a method that allows exponential amplification of circular DNA in a cell-free system.

BACKGROUND ART

The DNA cloning technology on which biotechnological development was based is a technique for amplifying circular DNA that had been prepared by cutting and pasting DNA fragments as plasmid in cells of *E. coli*, etc. A use of a DNA cloning technology that uses cells to amplify circular DNA necessitates troublesome procedures such as cell cultivation, extraction/purification of amplified products and the like. Also, the environment for experimenting such DNA cloning is limited, since it is necessary to prepare genetically modified organisms to perform DNA cloning that uses cells.

A common method used for amplifying DNA in vitro is polymerase chain reaction (PCR). However, an in vitro DNA amplification using PCR does not allow circular DNA to be amplified as it is. In vitro amplification methods of circular DNA include the rolling circle amplification (RCA) (NPL 1, PTL 1, PTL 2, PTL 3). However, if circular DNA is to be amplified using the rolling circle amplification, a primer specific to the target DNA would need to be designed each time. Furthermore, the amplification product that directly results from the rolling circle amplification is a linear DNA, so it would be necessary to perform an additional cyclization step to cyclize the obtained amplification product, such as incubating with a recombination enzyme. Another reported method is a method of obtaining a monomer replication product by separating a minichromosome of *E. coli* (oriC circular DNA) and then separating it to obtain a monomeric circular replication product has been reported (NPLs 2 to 5). However, with regard to the reaction conditions applied in these publications, it has been experimentally demonstrated that the replication efficiency of circular DNA molecules is only approximately 15 to 40% of the added template DNA, and thus that the amplified amount does not reach even double (NPLs 3 to 6). Furthermore, the size of circular DNA used as a template in these publications is only less than 10 kbp.

As shown above, amplification of circular DNA using the conventional in vitro DNA amplification was disadvantageous in that it required primers to be bonded with the template DNA, produced linear DNA as the amplification product, and limited the size of DNA that can be amplified to within a few kbp. Still further, there has been a problem that, when a circular amplification product intends to be produced using an *Escherichia coli* minichromosome replication system, template circular DNA cannot be amplified even to double.

CITATION LIST

Patent Literature

PTL 1: Japanese unexamined patent publication No. 2005-229950
PTL 2: Japanese unexamined patent publication No. 2008-161182
PTL 3 Japanese unexamined patent publication No. 2012-501173

Non Patent Literature

NPL 1: Fakruddin M et al., J Pharm Bioallied Sci. 2013, 5: 245-252
NPL 2: Peng H & Marians K J. PNAS. 1993, 90: 8571-8575
NPL 3: Hiasa H & Marians K J. J Biol Chem. 1994, 269: 32655-32659
NPL 4: Funnell B et al., J Biol Chem. 1986, 261: 5616-5624
NPL 5: Hiasa H et al., J Biol Chem. 1994, 269: 2093-2099
NPL 6: Hiasa H & Marians K J. J Biol Chem. 1994, 269: 26959-26968

SUMMARY OF INVENTION

Technical Problem

The object of the present invention is to provide a method for easily and exponentially amplifying circular DNA, especially long chain circular DNA, in a cell-free system.

Solution to Problem

The present inventors performed extensive studies to solve the above problem and found that the cycle of "initiation of replication (unwinding of DNA double strand)/elongation (progress of replication fork)/separation of replicated sister DNAs (Decatenation)" is repeated and exponential amplification of circular DNA is provided when circular DNA having a replication origin sequence (origin of chromosome (oriC)) is mixed with a reaction solution comprising:
  a first enzyme group that catalyzes replication of circular DNA;
  a second enzyme group that catalyzes an Okazaki fragment maturation and synthesizes two sister circular DNAs constituting a catenane;
  a third enzyme group that catalyzes a separation of two sister circular DNAs;
  a buffer;
  ATP;
  GTP, CTP and UTP;
  dNTP;
  a magnesium ion source; and
  an alkali metal ion source, thereby generating a reaction mixture.
  to form a reaction mixture, which is then reacted.

In other words, the present invention encompasses the following aspect without being limited thereby.

[1] A method for amplifying circular DNA, comprising the following steps: (1) forming a reaction mixture of circular DNA as a template with a reaction solution comprising:
  a first enzyme group that catalyzes replication of circular DNA;
  a second enzyme group that catalyzes an Okazaki fragment maturation and synthesizes two sister circular DNAs constituting a catenane;
  a third enzyme group that catalyzes a separation of two sister circular DNAs;
  a buffer;
  ATP;
  GTP, CTP and UTP;
  dNTP;
  a magnesium ion source; and
  an alkali metal ion source, wherein
  wherein the circular DNA includes a replication origin sequence (origin of chromosome (oriC)) that can bind to an enzyme having DnaA activity; and (2) retaining temperature of the reaction mixture formed in (1) under an isothermal condition.

[2] A method for amplifying circular DNA, comprising the following steps:
(1) forming a reaction mixture of circular DNA as a template with a reaction solution comprising:
a first enzyme group that catalyzes replication of circular DNA;
a second enzyme group that catalyzes an Okazaki fragment maturation and synthesizes two sister circular DNAs constituting a catenane;
a third enzyme group that catalyzes a separation of two sister circular DNAs;
a buffer;
ATP;
GTP, CTP and UTP;
dNTP;
a magnesium ion source; and
an alkali metal ion source, wherein
wherein the circular DNA includes a replication origin sequence (origin of chromosome (oriC)) that can bind to an enzyme having DnaA activity; and
(2) incubating the reaction mixture formed in step (1) in a temperature cycle of repeating an incubation at 30° C. or higher and an incubation at 27° C. or lower.

[3] The method according to the above [1] or [2], wherein the reaction solution further comprises a protein non-specific adsorption inhibitor and/or a nucleic acid non-specific adsorption inhibitor.

[4] The method according to the above [1] or [2], wherein the reaction solution further comprises linear DNA-specific exonuclease and/or RecG-type helicase.

[5] The method according to the above [1] or [2], wherein the reaction solution further comprises an ammonium salt.

[6] The method according to the above [1] or [2], wherein
the first enzyme group comprises a combination of an enzyme having DnaA activity, one or more types of nucleoid protein, an enzyme or enzyme group having DNA gyrase activity, single-strand binding protein (SSB), an enzyme having DnaB-type helicase activity, an enzyme having DNA helicase loader activity, an enzyme having DNA primase activity, an enzyme having DNA clamp activity, and an enzyme or enzyme group having DNA polymerase III* activity;
the second enzyme group comprises a combination of an enzyme having DNA polymerase I activity and an enzyme having DNA ligase activity, and
the third enzyme group comprises an enzyme having topoisomerase III activity and/or an enzyme having topoisomerase IV activity.

[7] The method according to the above [6], wherein the second enzyme group further comprises an enzyme having RNaseH activity.

[8] The method according to the above [6], wherein the third enzyme group further comprises an enzyme having RecQ-type helicase activity.

[9] The method according to the above [6], wherein
in the first enzyme group,
the one or more nucleoid proteins are IHF or HU,
the enzyme or the enzyme group having DNA gyrase activity is a complex of GyrA and GyrB,
the enzyme having DnaB-type helicase activity is DnaB helicase,
the enzyme having DNA helicase loader activity is DnaC helicase loader,
the enzyme having DNA primase activity is DnaG primase,
the enzyme having DNA clamp activity is DnaN clamp,
the enzyme or the enzyme group having DNA polymerase III* activity is an enzyme or an enzyme group comprising any of DnaX, HolA, HolB, HolC, HolD, DnaE, DnaQ, and HolE.

[10] The method according to the above [1], wherein the isothermal condition in step (2) is a constant temperature included in the range of 25° C. to 50° C.

[11] The method according to the above [1] or [2], wherein the reaction solution further comprises RecG-type helicase and/or single-strand DNA-specific exonuclease.

[12] The method according to the above [1] or [2], wherein the reaction solution further comprises linear DNA-specific exonuclease and/or single-strand DNA-specific exonuclease.

[13] The method according to the above [1] or [2], wherein the reaction solution further comprises a DNA stabilizing factor.

[14] The method according to the above [1] or [2], wherein
step (1) comprises:
(1-1) pre-incubating a reaction solution comprising:
a first enzyme group that catalyzes replication of circular DNA;
a second enzyme group that catalyzes an Okazaki fragment maturation and synthesizes two sister circular DNAs constituting a catenane;
a third enzyme group that catalyzes a separation of two sister circular DNAs;
a buffer;
ATP;
GTP, CTP and UTP;
dNTP;
a magnesium ion source; and
an alkali metal ion source; and
(1-2) forming a reaction mixture of the reaction solution with circular DNA as a template.

[15] The method according to the above [1] or [2], wherein step (2) is carried out in a water-in-oil emulsion.

[16] The method according to the above [1] or [2], wherein, following step (2), the method further comprises:
(3) performing a post-reaction treatment, wherein
the post-reaction treatment is:
(i) a treatment of diluting the reaction mixture five or more times with the reaction solution that does not contain the first to third enzyme groups, and then rewarming the resultant;
(ii) a treatment with linear DNA-specific exonuclease and/or single-strand DNA-specific exonuclease; and/or
(iii) a treatment with a gap repair enzyme.

[17] A composition for amplifying circular DNA, comprising:
a first enzyme group that catalyzes replication of circular DNA;
a second enzyme group that catalyzes an Okazaki fragment maturation and synthesizes two sister circular DNAs constituting a catenane;
a third enzyme group that catalyzes a separation of two sister circular DNAs;
a buffer;
ATP;
GTP, CTP and UTP;
dNTP;
a magnesium ion source; and
an alkali metal ion source.

[18] The composition according to the above [17], further comprising a protein non-specific adsorption inhibitor and/or a nucleic acid non-specific adsorption inhibitor.

[19] The composition according to the above [17], further comprising linear DNA-specific exonuclease and/or RecG-type helicase.

[20] The composition according to the above [17], further comprising RecG-type helicase and/or single-strand DNA-specific exonuclease.

[21] The composition according to the above [17], further comprising linear DNA-specific exonuclease and/or single-strand DNA-specific exonuclease.

[22] The composition according to the above [17], further comprising a DNA stabilizing factor.

[23] A kit for amplifying circular DNA, comprising a combination of: a first enzyme group that catalyzes replication of circular DNA;
  a second enzyme group that catalyzes an Okazaki fragment maturation and synthesizes two sister circular DNAs constituting a catenane;
  a third enzyme group that catalyzes a separation of two sister circular DNAs;
  a buffer;
  ATP;
  GTP, CTP and UTP;
  dNTP;
  a magnesium ion source; and
  an alkali metal ion source.

[24] The kit according to the above [23], further comprising a combination with a protein non-specific adsorption inhibitor and/or a nucleic acid non-specific adsorption inhibitor.

[25] The kit according to the above [23], further comprising a combination with linear DNA-specific exonuclease and/or RecG-type helicase.

[26] The kit according to the above [23], further comprising RecG-type helicase and/or single-strand DNA-specific exonuclease.

[27] The kit according to the above [23], further comprising linear DNA-specific exonuclease and/or single-strand DNA-specific exonuclease.

[28] The kit according to the above [23], further comprising a DNA stabilizing factor.

[29] The kit according to the above [23], further comprising a gap repair enzyme.

[30] A method for exponentially amplifying circular DNA by repeating a replication cycle, wherein the method comprises a step of forming a reaction mixture of a reaction solution comprising:
  a first enzyme group that catalyzes replication of circular DNA;
  a second enzyme group that catalyzes an Okazaki fragment maturation and synthesizes two sister circular DNAs constituting a catenane;
  a third enzyme group that catalyzes a separation of two sister circular DNAs;
  a buffer;
  ATP;
  GTP, CTP and UTP;
  dNTP;
  a magnesium ion source; and
  an alkali metal ion source, wherein
    wherein the circular DNA includes a replication origin sequence (origin of chromosome (oriC)) that can bind to an enzyme having DnaA activity.

[31] A method for amplifying circular DNA, comprising the following steps:
  (1) forming a reaction mixture of circular DNA as a template with a reaction solution comprising:
    a first enzyme group that catalyzes replication of circular DNA;
    a second enzyme group that catalyzes an Okazaki fragment maturation and synthesizes two sister circular DNAs constituting a catenane;
    a third enzyme group that catalyzes a separation of two sister circular DNAs;
    a buffer;
    ATP;
    GTP, CTP and UTP;
    dNTP;
    a magnesium ion source; and
    an alkali metal ion source, wherein
      wherein the circular DNA includes a replication origin sequence (origin of chromosome (oriC)) that can bind to an enzyme having DnaA activity; and
  (2) retaining temperature of the reaction mixture formed in (1) in a predetermined temperature range.

[32] A kit for amplifying circular DNA, comprising a combination of:
  a first enzyme group that catalyzes replication of circular DNA;
  a second enzyme group that catalyzes an Okazaki fragment maturation and synthesizes two sister circular DNAs constituting a catenane;
  a third enzyme group that catalyzes a separation of two sister circular DNAs;
  a buffer;
  ATP;
  GTP, CTP and UTP;
  dNTP;
  a magnesium ion source; and
  an alkali metal ion source, and an instruction manual including instructions for carrying out a method for exponentially amplifying circular DNA by repeatedly performing a replication cycle on a reaction mixture of a reaction solution comprising the above described combination and circular DNA serving as a template.

[33] The method according to any one of the above [1], [2], [30] and [31], wherein
  the reaction solution further comprises tRNA.

[34] The composition according to the above [17], wherein the reaction solution further comprises tRNA.

[35] The kit according to the above [23] or [32], wherein the reaction solution further comprises tRNA.

[36] The method according to any one of the above [1], [2], [30] and [31], wherein
  the reaction solution further comprises 100 mM or more of the alkali metal ion source.

[37] The composition according to the above [17], wherein the reaction solution further comprises 100 mM or more of the alkali metal ion source.

[38] The kit according to the above [23] or [32], wherein the reaction solution further comprises 100 mM or more of the alkali metal ion source.

[39] The method according to any one of the above [1], [2], [30] and [31], wherein the circular DNA is amplified at least 10 times.

Advantageous Effects of Invention

The present invention provides a method for easily and exponentially amplifying circular DNA, especially long chain circular DNA, without using *E. coli* cells or plasmid vectors. The present invention frees the circular DNA amplification from primers, and enables amplification of long chain circular DNA that exceeds 200 kb. According to the method of the present invention, circular DNA can be amplified even from only a single molecule of template circular DNA. Furthermore, the amplification product obtained by the present invention is a copy that maintains the circular structure of the original template. By adding DNA fragments to the reaction system after the DNA fragments had been ligated, the present invention also enables specific amplification of only the DNA that was cyclized by ligation.

BRIEF DESCRIPTION OF DRAWINGS

FIG. 4a shows the result of the amplification product at each reaction time in a case in which a long chain circular DNA of 200 kb (15 pM, 20 ng) was used as a template. FIG. 4b shows the result of the amplification product 3 h. after reaction in a case in which long chain circular DNAs of 80 kb (15 pM, 8 ng) and 200 kb (5 pM, 6.7 ng) were used as templates.

FIG. 6a shows the detection result of the amplification product in a case in which a circular DNA of 9.6 kb was used as a template, the detection result obtained by using SYBR Green after subjecting the product to agarose electrophoresis. FIG. 6b is a graph that depicts the result of the amplification level by quantifying the amount of DNA of the amplification product by using the PicoGreen method or by transforming E. coli.

FIG. 8a is a scheme of a dilution of a circular DNA mixture. FIG. 8b shows the detection result of the amplification product in a case in which a diluted mixture of circular DNA was amplified, the detection result obtained by using SYBR Green after subjecting the product to agarose electrophoresis.

FIG. 9a is a scheme of the experiment process. FIG. 9b shows the result in a case in which a passage amplification was repeated 10 times by diluting the DNA product after amplification to form a new reaction solution, then subjecting the solution to amplification again.

DESCRIPTION OF EMBODIMENTS

Figure 1:
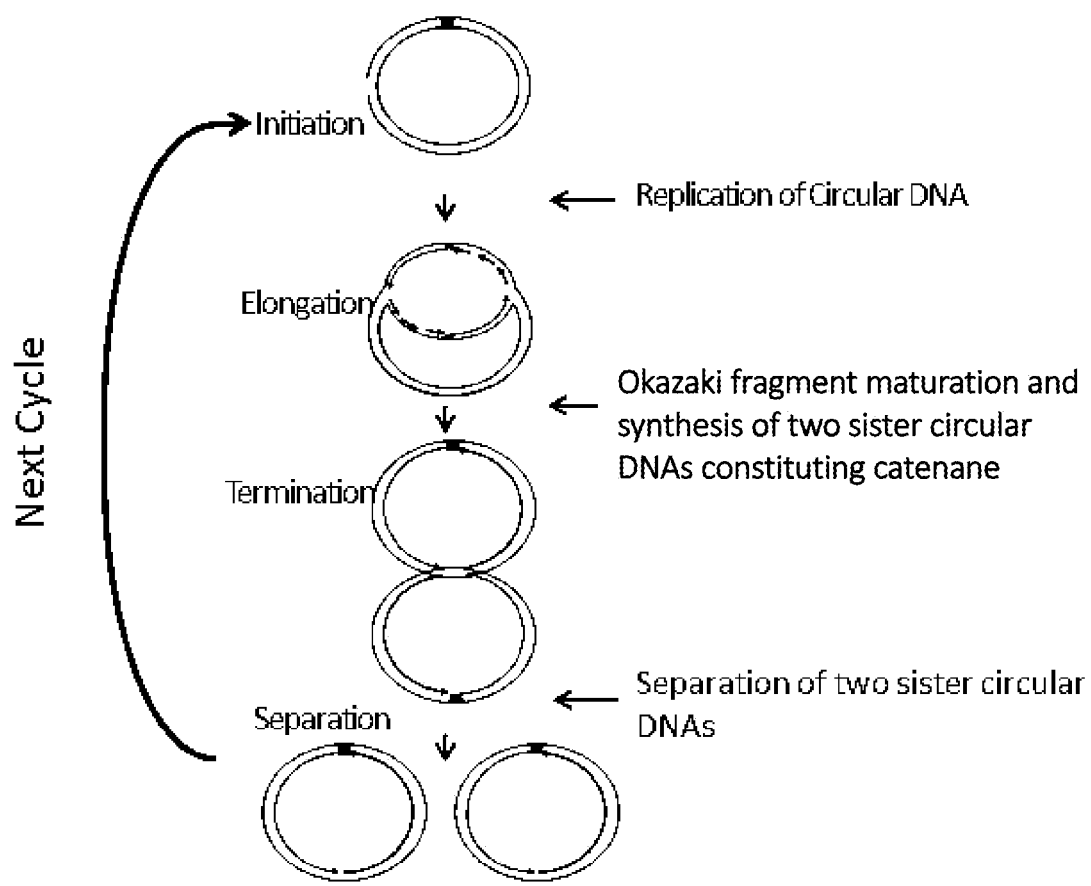
FIG. 1 shows a model of the replication cycle of the present invention.

Hereafter, the present invention will be specifically described. However, the present invention is not limited to the following descriptions. The scientific terms and technical terms used with regard to the present invention have meanings, which are commonly understood by a person skilled in the art, unless otherwise specified in the present description.

<Circular DNA>

The circular DNA that is used as the template is preferably a double-strand. The circular DNA used as the template is not particularly limited as long as it includes a replication origin sequence (origin of chromosome (oriC)) that can bind to an enzyme having DnaA activity, and examples include natural circular DNA such as a circular chromosome of microorganisms, circular DNA created by ligating natural circular DNA that had been cut off by enzyme processing, etc. with another DNA fragment and cyclizing the ligated product, and circular DNA that had been artificially synthesized altogether. With regards to replication origin sequences (origin of chromosome (oriC)) that can bind to an enzyme having DnaA activity (may be referred to hereinafter, simply as "replication origin sequence"), publicly known replication origin sequences existing in bacterium, such as E. coli, Bacillus subtilis, etc., may be obtained from a public database such as NCBI (the World Wide Web site at www.ncbi.nlm.nih.gov). Or else, the replication origin sequence may be obtained by cloning a DNA fragment that can bind to an enzyme having DnaA activity and analyzing its base sequence.

The circular DNA that is to be used as a template in the present invention may be circular DNA containing a replication origin sequence from the beginning, or circular DNA originally lacking a replication origin sequence but later incorporating a replication origin sequence.

The circular DNA that is used as a template in the present invention may include marker gene sequences that are resistant to drugs, such as kanamycin, ampicillin, tetracycline, etc. according to the purpose.

Furthermore, the circular DNA that is used as a template in the present invention may be in a purified state, or it may be in a form of a suspension of fungus body extraction including circular DNA. A single type of circular DNA may be used as a template, but it is also possible to use a mixture of several types of circular DNAs, such as a DNA library, in one test tube as a template.

There is no limit to the length of circular DNA used as a template in the present invention, and the length may be 1 kb (1,000 base length) or longer, 5 kb (5,000 base length) or longer, 8 kb (8,000 base length) or longer, 10 kb (10,000 base length) or longer, 50 kb (50,000 base length) or longer, 100 kb (100,000 base length) or longer, 200 kb (200,000 base length) or longer, 500 kb (500,000 base length) or longer, 1000 kb (1,000,000 base length) or longer, or 2000 kb (2,000,000 base length) or longer.

<First, Second and Third Enzyme Groups>

1. First Enzyme Group

In the present description, the first enzyme group means an enzyme group that catalyzes replication of circular DNA.

An example of a first enzyme group that catalyzes replication of circular DNA is an enzyme group set forth in Kaguni J M & Kornberg A. Cell. 1984, 38:183-90. Specifically, examples of the first enzyme group include one or more enzymes or enzyme group selected from a group consisting of an enzyme having DnaA activity, one or more types of nucleoid protein, an enzyme or enzyme group having DNA gyrase activity, single-strand binding protein (SSB), an enzyme having DnaB-type helicase activity, an enzyme having DNA helicase loader activity, an enzyme having DNA primase activity, an enzyme having DNA clamp activity, and an enzyme or enzyme group having DNA polymerase III* activity, and a combinations of all of the aforementioned enzymes or enzyme groups.

The enzyme having DnaA activity is not particularly limited in its biological origin as long as it has an initiator activity that is similar to that of DnaA, which is an initiator protein of E. coli, and DnaA derived from E. coli may be preferably used. The Escherichia coli-derived DnaA may be contained as a monomer in the reaction solution in an amount of 1 nM to 10 μM, preferably in an amount of 1 nM to 5 μM, 1 nM to 3 μM, 1 nM to 1.5 μM, 1 nM to 1.0 μM, 1 nM to 500 nM, 50 nM to 200 nM, or 50 nM to 150 nM, but without being limited thereby.

A nucleoid protein is protein in the nucleoid. The one or more types of nucleoid protein used in the present invention is not particularly limited in its biological origin as long as it has an activity that is similar to that of the nucleoid protein of E. coli. For example, Escherichia coli-derived IHF, namely, a complex of IhfA and/or IhfB (a heterodimer or a homodimer), or Escherichia coli-derived HU, namely, a complex of hupA and hupB can be preferably used. The Escherichia coli-derived IHF may be contained as a hetero/homo dimer in a reaction solution in a concentration range of 5 nM to 400 nM. Preferably, the Escherichia coli-derived IHF may be contained in a reaction solution in a concentration range of 5 nM to 200 nM, 5 nM to 100 nM, 5 nM to 50 nM, 10 nM to 50 nM, 10 nM to 40 nM, or 10 nM to 30 nM, but the concentration range is not limited thereto. The Escherichia coli-derived HU may be contained in a reaction solution in a concentration range of 1 nM to 50 nM, and preferably, may be contained therein in a concentration range of 5 nM to 50 nM or 5 nM to 25 nM, but the concentration range is not limited thereto.

An enzyme or enzyme group having DNA gyrase activity is not particularly limited in its biological origin as long as it has an activity that is similar to that of the DNA gyrase of

*E. coli.* For example, a complex of *Escherichia coli*-derived GyrA and GyrB can be preferably used. Such a complex of *Escherichia coli*-derived GyrA and GyrB may be contained as a heterotetramer in a reaction solution in a concentration range of 20 nM to 500 nM, and preferably, may be contained therein in a concentration range of 20 nM to 400 nM, 20 nM to 300 nM, 20 nM to 200 nM, 50 nM to 200 nM, or 100 nM to 200 nM, but the concentration range is not limited thereto.

A single-strand binding protein (SSB) is not particularly limited in its biological origin as long as it has an activity that is similar to that of the single-strand binding protein of *E. coli.* For example, *Escherichia coli*-derived SSB can be preferably used. Such *Escherichia coli*-derived SSB may be contained as a homotetramer in a reaction solution in a concentration range of 20 nM to 1000 nM, and preferably, may be contained therein in a concentration range of 20 nM to 500 nM, 20 nM to 300 nM, 20 nM to 200 nM, 50 nM to 500 nM, 50 nM to 400 nM, 50 nM to 300 nM, 50 nM to 200 nM, 50 nM to 150 nM, 100 nM to 500 nM, or 100 nM to 400 nM, but the concentration range is not limited thereto.

An enzyme having DnaB-type helicase activity is not particularly limited in its biological origin as long as it has an activity that is similar to that of the DnaB of *E. coli.*

For example, *Escherichia coli*-derived DnaB can be preferably used. Such *Escherichia coli*-derived DnaB may be contained as a homohexamer in a reaction solution in a concentration range of 5 nM to 200 nM, and preferably, may be contained therein in a concentration range of 5 nM to 100 nM, 5 nM to 50 nM, or 5 nM to 30 nM, but the concentration range is not limited thereto.

An enzyme having DNA helicase loader activity is not particularly limited in its biological origin as long as it has an activity that is similar to that of the DnaC of *E. coli.*

For example, *Escherichia coli*-derived DnaC can be preferably used. Such *Escherichia coli*-derived DnaC may be contained as a homohexamer in a reaction solution in a concentration range of 5 nM to 200 nM, and preferably, may be contained therein in a concentration range of 5 nM to 100 nM, 5 nM to 50 nM, or 5 nM to 30 nM, but the concentration range is not limited thereto.

An enzyme having DNA primase activity is not particularly limited in its biological origin as long as it has an activity that is similar to that of the DnaG of *E. coli.* For example, *Escherichia coli*-derived DnaG can be preferably used. Such *Escherichia coli*-derived DnaG may be contained as a monomer in a reaction solution in a concentration range of 20 nM to 1000 nM, and preferably, may be contained therein in a concentration range of 20 nM to 800 nM, 50 nM to 800 nM, 100 nM to 800 nM, 200 nM to 800 nM, 250 nM to 800 nM, 250 nM to 500 nM, or 300 nM to 500 nM, but the concentration range is not limited thereto.

An enzyme having DNA clamp activity is not particularly limited in its biological origin as long as it has an activity that is similar to that of the DnaN of *E. coli.* For example, *Escherichia coli*-derived DnaN can be preferably used. Such *Escherichia coli*-derived DnaN may be contained as a homodimer in a reaction solution in a concentration range of 10 nM to 1000 nM, and preferably, may be contained therein in a concentration range of 10 nM to 800 nM, 10 nM to 500 nM, 20 nM to 500 nM, 20 nM to 200 nM, 30 nM to 200 nM, or 30 nM to 100 nM, but the concentration range is not limited thereto.

An enzyme or enzyme group having DNA polymerase III* activity is not particularly limited in its biological origin as long as it is an enzyme or enzyme group having an activity that is similar to that of the DNA polymerase III* complex of *E. coli.* For example, an enzyme group comprising any of *Escherichia coli*-derived DnaX, HolA, HolB, HolC, HolD, DnaE, DnaQ, and HolE, preferably, an enzyme group comprising a complex of *Escherichia coli*-derived DnaX, HolA, HolB, and DnaE, and more preferably, an enzyme comprising a complex of *Escherichia coli*-derived DnaX, HolA, HolB, HolC, HolD, DnaE, DnaQ, and HolE, can be preferably used. Such an *Escherichia coli*-derived DNA polymerase III* complex may be contained as a heteromultimer in a reaction solution in a concentration range of 2 nM to 50 nM, and preferably, may be contained therein in a concentration range of 2 nM to 40 nM, 2 nM to 30 nM, 2 nM to 20 nM, 5 nM to 40 nM, 5 nM to 30 nM, or 5 nM to 20 nM, but the concentration range is not limited thereto.

2. Second Enzyme Group

In the present description, the second enzyme group means an enzyme group that that catalyzes an Okazaki fragment maturation and synthesizes two sister circular DNAs constituting a catenane.

In the present invention, the two sister circular DNAs constituting a catenane are two circular DNAs synthesized by DNA replication, then joined together.

Examples of second enzyme groups that catalyze an Okazaki fragment maturation and synthesize two sister circular DNAs constituting a catenane may include, for example, one or more enzymes selected from the group consisting of an enzyme having DNA polymerase I activity, an enzyme having DNA ligase activity, and an enzyme having RNaseH activity, or a combination of these enzymes.

An enzyme having DNA polymerase I activity is not particularly limited in its biological origin as long as it has an activity that is similar to DNA polymerase I of *E. coli.* For example, *Escherichia coli*-derived DNA polymerase I can be preferably used. Such *Escherichia coli*-derived DNA polymerase I may be contained as a monomer in a reaction solution in a concentration range of 10 nM to 200 nM, and preferably, may be contained therein in a concentration range of 20 nM to 200 nM, 20 nM to 150 nM, 20 nM to 100 nM, 40 nM to 150 nM, 40 nM to 100 nM, or 40 nM to 80 nM, but the concentration range is not limited thereto.

An enzyme having DNA ligase activity is not particularly limited in its biological origin as long as it has an activity that is similar to DNA ligase of *E. coli.* For example, *Escherichia coli*-derived DNA ligase or the DNA ligase of T4 phage can be preferably used. Such *Escherichia coli*-derived DNA ligase may be contained as a monomer in a reaction solution in a concentration range of 10 nM to 200 nM, and preferably, may be contained therein in a concentration range of 15 nM to 200 nM, 20 nM to 200 nM, 20 nM to 150 nM, 20 nM to 100 nM, or 20 nM to 80 nM, but the concentration range is not limited thereto.

The enzyme having RNaseH activity is not particularly limited in terms of biological origin, as long as it has the activity of decomposing the RNA chain of an RNA-DNA hybrid. For example, *Escherichia coli*-derived RNaseH can be preferably used. Such *Escherichia coli*-derived RNaseH may be contained as a monomer in a reaction solution in a concentration range of 0.2 nM to 200 nM, and preferably, may be contained therein in a concentration range of 0.2 nM to 200 nM, 0.2 nM to 100 nM, 0.2 nM to 50 nM, 1 nM to 200 nM, 1 nM to 100 nM, 1 nM to 50 nM, or 10 nM to 50 nM, but the concentration range is not limited thereto.

3. Third Enzyme Group

In the present description, the third enzyme group means an enzyme group that catalyzes a separation of two sister circular DNAs An example of a third enzyme group that catalyzes a separation of two sister circular DNAs is an enzyme group set forth in, for example, the enzyme group described in Peng H & Marians K J. PNAS. 1993, 90: 8571-8575. Specifically, examples of the third enzyme group include one or more enzymes selected from a group consisting of an enzyme having topoisomerase IV activity, an enzyme having topoisomerase III activity, and an enzyme having RecQ-type helicase activity; or a combination of the aforementioned enzymes.

The enzyme having topoisomerase III activity is not particularly limited in terms of biological origin, as long as it has the same activity as that of the topoisomerase III of *Escherichia coli*. For example, *Escherichia coli*-derived topoisomerase III can be preferably used. Such *Escherichia coli*-derived topoisomerase III may be contained as a monomer in a reaction solution in a concentration range of 20 nM to 500 nM, and preferably, may be contained therein in a concentration range of 20 nM to 400 nM, 20 nM to 300 nM, 20 nM to 200 nM, 20 nM to 100 nM, or 30 to 80 nM, but the concentration range is not limited thereto.

The enzyme having RecQ-type helicase activity is not particularly limited in terms of biological origin, as long as it has the same activity as that of the RecQ of *Escherichia coli*. For example, *Escherichia coli*-derived RecQ can be preferably used. Such *Escherichia coli*-derived RecQ may be contained as a monomer in a reaction solution in a concentration range of 20 nM to 500 nM, and preferably, may be contained therein in a concentration range of 20 nM to 400 nM, 20 nM to 300 nM, 20 nM to 200 nM, 20 nM to 100 nM, or 30 to 80 nM, but the concentration range is not limited thereto.

An enzyme having topoisomerase IV activity is not particularly limited in its biological origin as long as it has an activity that is similar to topoisomerase IV of *E. coli*. For example, *Escherichia coli*-derived topoisomerase IV that is a complex of ParC and ParE can be preferably used. Such *Escherichia coli*-derived topoisomerase IV may be contained as a heterotetramer in a reaction solution in a concentration range of 0.1 nM to 50 nM, and preferably, may be contained therein in a concentration range of 0.1 nM to 40 nM, 0.1 nM to 30 nM, 0.1 nM to 20 nM, 1 nM to 40 nM, 1 nM to 30 nM, 1 nM to 20 nM, 1 nM to 10 nM, or 1 nM to 5 nM, but the concentration range is not limited thereto.

The first, second and third enzyme groups given above may be those that are commercially available, or they may be extracted from microorganisms and purified as necessary. Extraction and purification of enzymes from microorganisms may be performed as necessary using means that are available to a person skilled in the art.

When enzymes other than the above described *Escherichia coli*-derived enzymes are used as the first, second and third enzyme groups, they may be each used in a concentration range corresponding, as an enzyme activity unit, to the concentration range that is specified with respect to the above described *Escherichia coli*-derived enzyme.

The reaction solution containing cell-free protein expression systems of the above mentioned enzymes may be mixed as-is with the circular DNA that constitutes a template to form a reaction mixture for amplifying circular DNA. The cell-free protein expression system may be a cell-free translation system that comprises a total RNA containing RNA consisting of a sequence that is complementary to the base sequence of genes encoding the above enzymes, mRNA or in vitro transcription product as the template RNA, or it may be a cell-free transcription/translation system that comprises genes encoding different enzymes or expression vectors including genes that encode different enzymes as the template DNA.

<Method for Amplifying Circular DNA>

The present invention relates to a method for amplifying circular DNA, comprising the following step:

(1) forming a reaction mixture of circular DNA as a template with a reaction solution comprising:
a first enzyme group that catalyzes replication of circular DNA;
a second enzyme group that catalyzes an Okazaki fragment maturation and synthesizes two sister circular DNAs constituting a catenane;
a third enzyme group that catalyzes a separation of two sister circular DNAs;
a buffer;
ATP;
GTP, CTP and UTP;
dNTP;
a magnesium ion source; and
an alkali metal ion source, wherein
wherein the circular DNA includes a replication origin sequence (origin of chromosome (oriC)) that can bind to an enzyme having DnaA activity.

In another embodiment, the method of the present invention may further comprise a step of pre-incubating the reaction solution, before the above described step (1). That is to say, the method of the present invention may be a method for amplifying circular DNA, comprising the following steps:

(1-1) pre-incubating a reaction solution comprising:
a first enzyme group that catalyzes replication of circular DNA;
a second enzyme group that catalyzes an Okazaki fragment maturation and synthesizes two sister circular DNAs constituting a catenane;
a third enzyme group that catalyzes a separation of two sister circular DNAs;
a buffer;
ATP;
GTP, CTP and UTP;
dNTP;
a magnesium ion source; and
an alkali metal ion source; and
(1-2) forming a reaction mixture of the reaction solution with circular DNA as a template,
wherein the circular DNA includes a replication origin sequence (origin of chromosome (oriC)) that can bind to an enzyme having DnaA activity. The pre-incubation may be carried out by retaining the temperature of the reaction solution, for example, in a temperature range of 0 to 40° C., 10 to 40° C., 15 to 37° C., or 16 to 30° C., for 5 to 60 minutes, 5 to 45 minutes, 5 to 30 minutes, 15 to 60 minutes, 15 to 45 minutes, or 15 to 30 minutes. In the pre-incubation, the temperature of the reaction solution may be somewhat fluctuated, if the temperature of the reaction solution is kept in the above described temperature range.

Without being limited by theory, in the present invention, a replication cycle is repeated as shown in FIG. 1, so that circular DNA can be exponentially amplified. In the present invention, the aforementioned circular DNA is used as a template, and it can be amplified at least 10 times, 50 times, 100 times, 200 times, 500 times, 1000 times, 2000 times, 3000 times, 4000 times, 5000 times, or 10000 times.

Circular DNA to be mixed with the reaction solution is as described in the above section <circular DNA>. The amount of template DNA used per reaction is not particularly limited. For example, at the initiation of the reaction, the circular DNA may be present in a concentration of 10 ng/µl or less, 5 ng/µl or less, 1 ng/µl or less, 0.8 ng/µl or less, 0.5 ng/µl or less, or 0.3 ng/µl or less, in the reaction solution. Moreover, at the initiation of the reaction, one molecule of circular DNA per reaction is allowed to be present as a template, so that it can be used in amplification.

The buffer contained in the reaction solution is not particularly limited, as long as it is suitably used in a pH range of pH 7 to 9, and preferably at pH 8. Examples of the buffer may include Tris-HCl, Tris-OAc, Hepes-KOH, a phosphate buffer, MOPS-NaOH, and Tricine-HCl. A preferred buffer is Tris-HCl or Tris-OAc. The concentration of the buffer can be selected, as appropriate, by a person skilled in the art, and thus, it is not particularly limited. In the case of Tris-HCl or Tris-OAc, for example, a concentration of 10 mM to 100 mM, 10 mM to 50 mM, or 20 mM can be selected.

ATP means adenosine triphosphate. At the initiation of the reaction, the concentration of ATP contained in the reaction solution may be in a range of, for example, 0.1 mM to 3 mM, and preferably in a concentration range of 0.1 mM to 2 mM, 0.1 mM to 1.5 mM, or 0.5 mM to 1.5 mM.

GTP, CTP and UTP mean guanosine triphosphate, cytidine triphosphate and uridine triphosphate, respectively. At the initiation of the reaction, the concentrations of GTP, CTP and UTP contained in the reaction solution may independently be, for example, in a range of 0.1 mM to 3.0 mM, and preferably in a concentration range of 0.5 mM to 3.0 mM or 0.5 mM to 2.0 mM.

dNTP is a general term for deoxyadenosine triphosphate (dATP), deoxyguanosine triphosphate (dGTP), deoxycytidine triphosphate (dCTP), and deoxythymidine triphosphate (dTTP). At the initiation of the reaction, the concentration of dNTP contained in the reaction solution may be, for example, in a range of 0.01 to 1 mM, and preferably in a concentration range of 0.05 mM to 1 mM or 0.1 mM to 1 mM.

The magnesium ion source is a substance that gives magnesium ions ($Mg^{2+}$) into the reaction solution. Examples of the magnesium ion source may include $Mg(OAc)_2$, $MgCl_2$, and $MgSO_4$. A preferred magnesium ion source is $Mg(OAc)_2$. At the initiation of the reaction, the concentration of the magnesium ion source contained in the reaction solution may be, for example, a concentration that is necessary for giving 5 to 50 mM magnesium ions into the reaction solution.

The alkali metal ion source is a substance that gives alkali metal ions into the reaction solution. Examples of the alkali metal ion may include sodium ions ($Na^+$) and potassium ions ($K+$). Examples of the alkali metal ion source may include potassium glutamate, potassium aspartate, potassium chloride, potassium acetate, sodium glutamate, sodium aspartate, sodium chloride, and sodium acetate. A preferred alkali metal ion source is potassium glutamate or potassium acetate. At the initiation of the reaction, the concentration of the alkali metal ion source contained in the reaction solution may be a concentration that is necessary for giving alkali metal ions in a range of 100 mM or more, and preferably 100 mM to 300 mM, into the reaction solution, but the concentration is not limited thereto. Keeping a good balance with earlier applications, 150 mM may be subtracted from the concentration of the above described alkali metal ion source.

The reaction solution used in the method of the present invention may further comprise a protein non-specific adsorption inhibitor or a nucleic acid non-specific adsorption inhibitor. Preferably, the reaction solution may further comprise a protein non-specific adsorption inhibitor and a nucleic acid non-specific adsorption inhibitor. Because of the presence of such a protein non-specific adsorption inhibitor and/or a nucleic acid non-specific adsorption inhibitor in the reaction solution, the reaction efficiency is improved. It is considered that the protein non-specific adsorption inhibitor and/or the nucleic acid non-specific adsorption inhibitor suppress non-specific adsorption between proteins and/or between a protein and circular DNA, or adhesion of a protein and circular DNA onto the surface of a vessel, so that the reaction efficiency can be improved.

The protein non-specific adsorption inhibitor is a protein that is irrelevant to the amplification reaction in the method of the present invention. Examples of such a protein may include bovine serum albumin (BSA), lysozyme, gelatin, heparin, and casein. The protein non-specific adsorption inhibitor may be contained in the reaction solution in a concentration range of 0.02 to 2.0 mg/ml, and preferably in a concentration range of 0.1 to 2.0 mg/ml, 0.2 to 2.0 mg/ml, or 0.5 to 2.0 mg/ml, but the concentration range is not limited thereto.

The nucleic acid non-specific adsorption inhibitor is a nucleic acid molecule or a nucleic acid-like factor that is irrelevant to the amplification reaction in the method of the present invention. Examples of such a nucleic acid molecule or a nucleic acid-like factor may include tRNA (transfer RNA), rRNA (ribosomal RNA), mRNA (messenger RNA), glycogen, heparin, oligo DNA, poly(I-C) (polyinosine-polycytidine), poly(dI-dC) (polydeoxyinosine-polydeoxycytidine), poly(A) (polyadenine), and poly(dA) (polydeoxyadenine). The nucleic acid non-specific adsorption inhibitor may be contained in the reaction solution in a concentration range of 1 to 500 ng/µl, and preferably in a concentration range of 10 to 500 ng/µl, 10 to 200 ng/µl, or 10 to 100 ng/µl, but the concentration range is not limited thereto. Keeping a good balance with earlier applications, when tRNA is selected as such a nucleic acid non-specific adsorption inhibitor, 50 ng/µl may be subtracted from the concentration of tRNA.

The reaction solution used in the method of the present invention may further comprise a DNA stabilizing factor. It is considered that because of the presence of such a DNA stabilizing factor in the reaction solution, the cleavage of DNA can be suppressed, and template DNA and an amplification product can be protected. Addition of the DNA stabilizing factor leads to the improvement of the yield of a product of interest. In particular, when the template DNA is long-chain circular DNA, since the template DNA and the amplification product are easily decomposed, addition of the DNA stabilizing factor is advantageous. The DNA stabilizing factor is not particularly limited. The DNA stabilizing factor may be selected from the group consisting of glucose, sucrose, dimethyl sulfoxide (DMSO), bovine serum albumin (BSA), ethylene glycol tetraacetic acid (EGTA), bathocuproin disulfonic acid disodium (BDA), penicillamine, Tiron (1,2-dihydroxybenzene-3,5-sulfonate), diethylenetriamine pentaacetic acid (DTPA), ethylenediamine tetraacetic acid (EDTA), a Dps protein (derived from *Escherichia coli*), and a metallothionein protein (derived from human). Among these, since DTPA, Tiron, BDA, a Dps protein and BSA have an action to promote a circular DNA amplification reaction, these are particularly preferable. DTPA or Tiron may be contained in the reaction solution in a concentration range of 0.01 mM to 0.3 mM, and preferably in a concentration range of 0.05 to 0.15 mM, but the concentration range is not limited thereto. BDA may be contained in the reaction solution in a concentration range of 0.01 to 0.5 mM, and preferably in a concentration range of 0.05 to 0.3 mM, but the concentration range is not limited thereto.

The Dps protein may be contained in the reaction solution in a concentration range of 0.3 to 3.0 µM, and preferably in a concentration range of 0.3 to 1.5 µM, but the concentration range is not limited thereto. BSA may be contained in the reaction solution in a concentration range of 0.02 to 2.0 mg/ml, and preferably in a concentration range of 0.1 to 2.0 mg/ml, 0.2 to 2.0 mg/ml, or 0.5 to 2.0 mg/ml, but the concentration range is not limited thereto.

The reaction solution used in the method of the present invention may further comprise linear DNA-specific exonuclease or RecG-type helicase. Preferably, the reaction solution may further comprise linear DNA-specific exonuclease and RecG-type helicase. Because of the presence of the linear DNA-specific exonuclease and/or the RecG-type helicase in the reaction solution, these enzymes provide the effects of reducing the amount of linear DNA generated as a result of duplex cleavage or the like during the amplification reaction, and improving the yield of a supercoiled product of interest.

The reaction solution used in the method of the present invention may further comprise RecG-type helicase or single-strand DNA-specific exonuclease. Preferably, the reaction solution may further comprise RecG-type helicase and single-strand DNA-specific exonuclease. Because of the presence of the RecG-type helicase and/or the single-strand DNA-specific exonuclease in the reaction solution, these enzymes provide the effects of reducing the amount of a low-molecular-weight amplification product generated as a by-product during the amplification reaction, and improving the yield of a supercoiled product of interest.

The reaction solution used in the method of the present invention may further comprise linear DNA-specific exonuclease or single-strand DNA-specific exonuclease. Preferably, the reaction solution may further comprise linear DNA-specific exonuclease and single-strand DNA-specific exonuclease. Because of the presence of the linear DNA-specific exonuclease and/or the single-strand DNA-specific exonuclease in the reaction solution, these enzymes provide the effects of reducing the amount of linear DNA generated as a result of duplex cleavage or the like during the amplification reaction, and improving the yield of a supercoiled product of interest.

The linear DNA-specific exonuclease is an enzyme that successively hydrolyzes linear DNA from the 5'-terminus or 3'-terminus thereof. The linear DNA-specific exonuclease is not particularly limited in terms of type or biological origin, as long as it has the activity of successively hydrolyzing linear DNA from the 5'-terminus or 3'-terminus thereof. For example, RecBCD, λ exonuclease, exonuclease III, exonuclease VIII, T5 exonuclease, T7 exonuclease, and Plasmid-Safe™ ATP-Dependent DNase (epicentre) can be used. A preferred linear DNA-specific exonuclease is RecBCD. The linear DNA exonuclease may be contained in the reaction solution in a concentration range of 0.001 to 1.0 U/µL, and preferably in a concentration range of 0.005 U to 1.0 U/µL, 0.01 to 1.0 U/µl, 0.05 to 1.0 U/µL, or 0.1 to 1.0 U/µl, but the concentration range is not limited thereto. The enzyme activity unit (U) of the linear DNA exonuclease is a unit obtained when the amount of enzyme necessary for converting 1 nmol deoxyribonucleotide of linear DNA to be acid-soluble during a reaction at 37° C. for 30 minutes is set at 1 U.

The RecG-type helicase is an enzyme that is considered to be helicase overcoming a DNA structure generated as a by-product by collision between replication folks at the termination of the elongation reaction. The RecG-type helicase is not particularly limited in terms of biological origin, as long as it has the same activity as that of Escherichia coli-derived RecG. For example, the Escherichia coli-derived RecG can be preferably used.

The Escherichia coli-derived RecG may be contained as a monomer in the reaction solution in a concentration range of 100 nM to 800 nM, and preferably in a concentration range of 100 nM to 500 nM, 100 nM to 400 nM, or 100 nM to 300 nM, but the concentration range is not limited thereto. The RecG-type helicase may be used in a concentration range corresponding, as an enzyme activity unit, to the concentration range that is specified with respect to the above described Escherichia coli-derived RecG.

The single-strand DNA-specific exonuclease is an enzyme that successively hydrolyzes the nucleotides at the 5'-terminus or 3'-terminus of single-strand DNA. The single-strand DNA-specific exonuclease is not particularly limited in terms of type or biological origin, as long as it has the activity of successively hydrolyzing the nucleotides at the 5'-terminus or 3'-terminus of single-strand DNA. For example, exonuclease 1 (exo I), RecJ, and exonuclease T can be used. A preferred single-strand DNA-specific exonuclease is exo I. The single-strand DNA-specific exonuclease may be contained in the reaction solution in a concentration range of 0.1 to 1.0 U/µl, and preferably in a concentration range of 0.15 to 1.0 U/µl, 0.2 to 1.0 U/µL, or 0.2 to 0.5 U/µL, but the concentration range is not limited thereto. The enzyme activity unit (U) of exo I is a unit obtained when the amount of enzyme necessary for converting 10 nmol deoxyribonucleotide of single-strand DNA to be acid-soluble during a reaction at 37° C. for 30 minutes is set at 1 U. The enzyme activity unit (U) of RecJ is a unit obtained when the amount of enzyme necessary for converting 0.05 nmol deoxyribonucleotide of single-strand DNA to be acid-soluble during a reaction at 37° C. for 30 minutes is set at 1 U.

The reaction solution used in the method of the present invention may further comprise an ammonium salt. Examples of the ammonium salt may include ammonium sulfate, ammonium chloride, and ammonium acetate. A particularly preferred ammonium salt is ammonium sulfate or ammonium acetate. The ammonium salt may be contained in the reaction solution in a concentration range of 0.1 mM to 100 mM, and preferably in a concentration range of 0.1 mM to 50 mM, 1 mM to 50 mM, or 1 mM to 20 mM, but the concentration range is not limited thereto.

When the Escherichia coli-derived DNA ligase that is an enzyme having DNA ligase activity is used as an enzyme belonging to the second enzyme group, its cofactor, NAD (nicotinamide adenine dinucleotide) is contained in the reaction solution. NAD may be contained in the reaction solution in a concentration range of 0.01 mM to 1.0 mM, and preferably in a concentration range of 0.1 mM to 1.0 mM, or 0.1 mM to 0.5 mM, but the concentration range is not limited thereto.

The reaction solution used in the method of the present invention may further comprise a reducing agent. Examples of a preferred reducing agent may include DTT, β-mercaptoethanol (2-mercaptoethanol), tris(2-carboxyethyl)phosphine (TCEP), and glutathione. A preferred reducing agent is DTT. The reducing agent may be contained in the reaction solution in a concentration of 1.0 mM to 15.0 mM, and preferably in a concentration range of 2.0 mM to 10.0 mM or 4.0 mM to 8.0 mM.

The reaction solution used in the method of the present invention may further comprise an enzyme and a substrate, which are used for regeneration of ATP. Examples of a combination of an enzyme and a substrate in an ATP regenerating system may include creatine kinase and creatine phosphate, and pyruvate kinase and phosphoenolpyruvate. The enzyme in the ATP regenerating system is, for example, myokinase. A preferred combination of the enzyme and the substrate in the ATP regenerating system is creatine kinase and creatine phosphate.

The first, second and third enzyme groups contained in the reaction solution are as described in the above section <First, second and third enzyme groups>.

In a certain embodiment, the first enzyme group used in the method of the present invention may include a combination of, an enzyme having DnaA activity, one or more nucleoid proteins, an enzyme or an enzyme group having DNA gyrase activity, a single-strand DNA binding protein (SSB), an enzyme having DnaB-type helicase activity, an enzyme having DNA helicase loader activity, an enzyme having DNA primase activity, an enzyme having DNA clamp activity, and an enzyme or an enzyme group having DNA polymerase III* activity. Herein, the one or more nucleoid proteins may be IHF or HU, the enzyme or the enzyme group having DNA gyrase activity may be a complex of GyrA and GyrB, the enzyme having DnaB-type helicase activity may be DnaB helicase, the enzyme having DNA helicase loader activity may be a DnaC helicase loader, the enzyme having DNA primase activity may be DnaG primase, the enzyme having DNA clamp activity may be a DnaN clamp, and the enzyme or the enzyme group having DNA polymerase III* activity may be an enzyme or an enzyme group comprising any of DnaX, HolA, HolB, HolC, HolD, DnaE, DnaQ, and HolE.

In another embodiment, the second enzyme group used in the method of the present invention may include a combination of an enzyme having DNA polymerase I activity and an enzyme having DNA ligase activity. Otherwise, the second enzyme group may include a combination of an enzyme having DNA polymerase I activity, an enzyme having DNA ligase activity, and an enzyme having RNaseH activity.

In a further embodiment, the third enzyme group used in the method of the present invention may include an enzyme having topoisomerase III activity and/or an enzyme having topoisomerase IV activity. Otherwise, the third enzyme group may include a combination of an enzyme having topoisomerase III activity and an enzyme having RecQ-type helicase activity. Otherwise, the third enzyme group may also be a combination of an enzyme having topoisomerase III activity, an enzyme having RecQ-type helicase activity, and an enzyme having topoisomerase IV activity.

The method of the present invention may further comprise, as step (2), a step of retaining temperature of the above described reaction mixture in a predetermined temperature range. Such a predetermined temperature range is not particularly limited, as long as it is a temperature range in which the DNA replication reaction can progress. For example, the predetermined temperature range may be a range of 20° C. to 80° C., 25° C. to 50° C., or 25° C. to 40° C., which is the optimal temperature of DNA polymerase. Retaining temperature in a predetermined temperature range permits a temperature change or a temperature fluctuation in the predetermined temperature range during the reaction. In a preferred embodiment, the above described step (2) may be a step of retaining temperature of the above described reaction mixture under an isothermal condition. Such isothermal conditions are not particularly limited, as long as the DNA replication reaction can progress under the conditions. For example, the isothermal conditions may be a constant temperature included in a range of 20° C. to 80° C., or in a range of 25° C. to 50° C., or in a range of 25° C. to 40° C., or at approximately 30° C., which is the optimal temperature of DNA polymerase. In the present description, the terms "retaining under an isothermal condition" and "reacting at an isothermal condition" mean that the temperature is kept in a temperature range of ±7° C., ±5° C., ±3° C., or ±1° C., with respect to the temperature, which is set during the reaction. The time for retaining temperature can be determined, as appropriate, depending on the amount of an amplification product of circular DNA of interest. The retaining time can be set to be, for example, 1 to 24 hours.

Alternatively, the method of the present invention may further comprise, as step (2), a step of incubating the above described reaction mixture in a temperature cycle of repeating incubation at 30° C. or higher and incubation at 27° C. or lower. The incubation at 30° C. or higher is not particularly limited, as long as the temperature is in a temperature range capable of initiating the replication of circular DNA comprising oriC. For example, the temperature may be 30 to 80° C., 30 to 50° C., 30 to 40° C., or 37° C. The incubation at 30° C. or higher may be carried out for 10 seconds to 10 minutes per cycle, although it is not particularly limited thereto. The incubation at 27° C. or lower is not particularly limited, as long as it is a temperature, at which initiation of replication is suppressed and the elongation reaction of DNA progresses. For example, the temperature may be 10 to 27° C., 16 to 25° C., or 24° C.

The incubation at 27° C. or lower may be preferably determined depending on the length of circular DNA to be amplified, but is not particularly limited thereto. For example, the incubation may be carried out for 1 to 10 seconds per 1000 bases in a single cycle. The number of temperature cycles is not particularly limited, but may be 10 to 50 cycles, 20 to 40 cycles, 25 to 35 cycles, or 30 cycles.

In a certain embodiment, step (2) may be carried out in a water-in-oil emulsion. The water-in-oil emulsion can be prepared by mixing mineral oil and a surfactant into the reaction mixture formed in step (1). The type and amount of the mineral oil and the surfactant can be determined, as appropriate, by a person skilled in the art.

The method of the present invention may further comprise, after completion of step (2), a step of diluting the reaction mixture five or more times with the reaction solution that does not contain the first to third enzyme groups, and then rewarming the resultant. Initiation of novel replication is suppressed by dilution of the enzyme groups, and at the same time, replication elongation, catenane formation, and a separation reaction, which are ongoing, continuously progress by the effects of the residual enzymes. In addition, by-products generated due to nicks and the like during the reaction can be repaired by the effects of the residual ligase and the like in this process. Therefore, the transition of amplification intermediates or by-products to final products is specifically induced, so that it can be expected that the yield of circular DNA having a supercoiled structure of interest will be improved.

The method of the present invention may further comprise, after completion of step (2), a step of treating the reaction mixture with linear DNA-specific exonuclease and/or single-strand DNA-specific exonuclease. By treating the reaction mixture with the linear DNA-specific exonuclease and/or the single-strand DNA-specific exonuclease, linear DNA generated as a by-product during the amplification reaction can be decomposed and removed.

The type and used amount of the linear DNA-specific exonuclease and/or the single-strand DNA-specific exonuclease may be as mentioned above. The treatment with the linear DNA-specific exonuclease and/or the single-strand DNA-specific exonuclease may be carried out, for example, at 25° C. to 40° C. for 30 minutes to 3 hours.

The method of the present invention may further comprise, after completion of step (2), a step of treating the reaction mixture with a gap repair enzyme. The gap repair enzyme is an enzyme group that repairs a gap, which is a loss of one or more contiguous nucleotides in double-strand DNA, or a nick, which is a cleavage of a phosphatediester bond between adjacent nucleotides in double-strand DNA, so as to form a complete double-strand supercoiled DNA. By treating the reaction mixture with the gap repair enzyme, DNA containing a gap or a nick, which has been generated as a by-product during the amplification reaction, is repaired, so that the effect of improving the yield of a supercoiled product of interest can be obtained.

The gap repair enzyme is not particularly limited in terms of type or biological origin, as long as it is an enzyme group capable of repairing the gap or nick of double-strand DNA. For example, a combination of, exonuclease III, DNA polymerase I, DNA ligase, and an enzyme or an enzyme group having DNA gyrase activity, can be used. The enzyme having exonuclease III activity may be used in a concentration of 5 to 100 mU/μL, but is not limited thereto. The enzyme activity unit (U) of exonuclease III is a unit obtained when the amount of enzyme necessary for converting 1 nmol deoxyribonucleotide of double-strand DNA to be acid-soluble during a reaction at 37° C. for 30 minutes is set at 1 U. The DNA polymerase I, the DNA ligase, and the enzyme or the enzyme group having DNA gyrase activity may be each used in a concentration determined in the aforementioned first or second enzyme group, but is not limited thereto. The treatment with a gap repair enzyme may be carried out, for example, at 25 to 40° C. for 5 to 120 minutes, and preferably, for 10 to 60 minutes.

The method of the present invention may include after completion of step (2), a step of purifying the amplification product of circular DNA as required according to the purpose.

The purification of circular DNA may be performed as necessary using means available to a person skilled in the art.

The circular DNA that had been amplified using the method of the present invention may be put to use for subsequent purposes, such as transformation, in the form of a reaction mixture after reaction as it is, or in a purified form of the reaction mixture.

<Composition and Kit for Amplifying Circular DNA>

The present invention also relates to a composition for amplifying circular DNA, comprising:
- a first enzyme group that catalyzes replication of circular DNA;
- a second enzyme group that catalyzes an Okazaki fragment maturation and synthesizes two sister circular DNAs constituting a catenane;
- a third enzyme group that catalyzes a separation of two sister circular DNAs;
- a buffer;
- ATP;
- GTP, CTP and UTP;
- dNTP;
- a magnesium ion source; and
- an alkali metal ion source.

The composition of the present invention may further comprise one or more components selected from a protein non-specific adsorption inhibitor, a nucleic acid non-specific adsorption inhibitor, linear DNA-specific exonuclease, RecG-type helicase, single-strand DNA-specific exonuclease, an ammonium salt, NAD, a reducing agent, a DNA stabilizing factor, and a combination of an enzyme and a substrate in the ATP regenerating system.

Specific type and concentration of the components contained in the composition of the present invention are as described in the above sections <Circular DNA>, <First, second and third enzyme groups>, and <Method for amplifying circular DNA>.

Moreover, the present invention also relates to a kit for amplifying circular DNA, comprising a combination of:
- a first enzyme group that catalyzes replication of circular DNA;
- a second enzyme group that catalyzes an Okazaki fragment maturation and synthesizes two sister circular DNAs constituting a catenane;
- a third enzyme group that catalyzes a separation of two sister circular DNAs;
- a buffer;
- ATP;
- GTP, CTP and UTP;
- dNTP;
- a magnesium ion source; and
- an alkali metal ion source.

The kit of the present invention may be one kit comprising all of the above described constitutional components. Otherwise, if the kit of the present invention is a kit for the purpose of being utilized in the method of the present invention, it may not comprise some of the above described constitutional components. When the present kit is a kit that does not comprise some of the above described constitutional components, a practitioner may add necessary components to the kit upon amplification, so as to carry out the amplification method of the present invention.

The kit of the present invention may further comprise additional constitutional components comprising one or more components selected from a protein non-specific adsorption inhibitor, a nucleic acid non-specific adsorption inhibitor, linear DNA-specific exonuclease, RecG-type helicase, single-strand DNA-specific exonuclease, an ammonium salt, NAD, a reducing agent, a DNA stabilizing factor, and a combination of an enzyme and a substrate in the ATP regenerating system. Moreover, for the treatment following the amplification reaction, the kit of the present invention may further comprise additional constitutional components comprising one or more components selected from linear DNA-specific exonuclease, single-strand DNA-specific exonuclease, and a gap repair enzyme. Such additional constitutional components may be included as a single kit in the kit of the present invention, or they may be provided as another kit, which is on premise of being used together with the kit of the present invention.

The specific component and concentration of each constitutional component included in the kit of the present invention are as described in the above sections <Circular DNA>, <First, second and third enzyme groups>, and <Method for amplifying circular DNA>.

The kit of the present invention may include a mixture of the above described constitutional components, which is packaged as a single item. Otherwise, the kit of the present invention may include the above described constitutional components, which are each packaged separately, or the kit of the present invention may also include several types of constitutional components, which are gathered or mixed, and then packaged.

Furthermore, the kit of the present invention may include an instruction manual including instructions for carrying out the method for amplifying circular DNA of the present invention. In this instruction manual, the matters described in the above sections <Circular DNA>, <First, second and third enzyme group>, and <Method for amplifying circular DNA> may be described as instructions.

EXAMPLES

The present invention is explained specifically based on the EXAMPLES. Note that the present invention is not limited to the range set forth in the following Examples.

Example 1: Amplification of Circular DNA

<Ingredient and Method>

After adding the template DNA to the reaction solution of the constitution shown in Table 1 and mixing them on ice, the temperature was retained at 30° C. for 1 h., 2 h. or 3 h. by an incubator. The mixture was prepared so that the total volume for each reaction was 10 microliter. After carrying out the reaction at 30° C., the reaction product was subjected to agarose electrophoresis (0.5% 1×TAE, 150 V, 100 min., 14° C.), then DNA was detected by using SYBR Green (Takara Bio Inc.).

TABLE 1

| Reaction buffer | |
|---|---|
| Tris-HCl (pH 8.0) | 20 mM |
| Dithiothreitol | 8 mM |
| Potassium glutamate | 150 mM |
| Mg(OAc)$_2$ | 10 mM |
| Creatine phosphate | 4 mM |
| rNTPs | 1 mM each |
| NAD | 0.25 mM |
| Ammonium sulfate | 10 mM |
| tRNA | 50 ng/µL |
| Bovine serum albumin (BSA) | 0.5 mg/ml |
| dNTPs | 0.1 mM each |
| Creatine kinase | 20 ng/µL |
| Enzyme group | |
| SSB | 400 nM |
| IHF | 40 nM |
| DnaG | 400 nM |
| DnaN | 40 nM |
| PolIII* | 5 nM |
| DnaB, DnaC | 20 nM |
| DnaA | 100 nM |
| RNaseH | 10 nM |
| Ligase | 50 nM |
| PolI | 50 nM |
| GyrA, GyrB | 50 nM |
| Topo IV | 5 nM |
| Topo III | 50 nM |
| RecQ | 50 nM |

In the table, SSB indicates SSB derived from *E. coli*, IHF indicates a complex of IhfA and IhfB derived from *E. coli*, DnaG indicates DnaG derived from *E. coli*, DnaN indicates DnaN derived from *E. coli*, PolIII* indicates DNA polymerase III* complex consisting of a complex of DnaX, HolA, HolB, HolC, HolD, DnaE, DnaQ, and HolE, DnaB indicates DnaB derived from *E. coli*, DnaC indicates DnaC derived from *E. coli*, DnaA indicates RNaseH derived from *E. coli*, Ligase indicates DNA ligase derived from *E. coli*, PolI indicates DNA polymerase I derived from *E. coli*, GyrA indicates GyrA derived from *E. coli*, GyrB indicates GyrB derived from *E. coli*, Topo IV indicates a complex of ParC and ParE derived from *E. coli*, Topo III indicates topoisomerase III derived from *E. coli*, and RecQ indicates RecQ derived from *E. coli*.

SSB was prepared by purifying an *E. coli* strain expressing SSB by steps that include ammonium sulfate precipitation and ion-exchange column chromatography.

IHF was prepared by purifying an *E. coli* strain coexpressing IhfA and IhfB by steps that include ammonium sulfate precipitation and affinity column chromatography.

DnaG was prepared by purifying an *E. coli* strain expressing DnaG by steps that include ammonium sulfate precipitation and anion-exchange column chromatography and gel filtration column chromatography.

DnaN was prepared by purifying an *E. coli* strain expressing DnaN by steps that include ammonium sulfate precipitation and anion-exchange column chromatography.

PolIII* was prepared by purifying an *E. coli* strain coexpressing DnaX, HolA, HolB, HolC, HolD, DnaE, DnaQ, and HolE by steps that include ammonium sulfate precipitation, affinity column chromatography and gel filtration column chromatography.

DnaB and DnaC were prepared by purifying an *E. coli* strain coexpressing DnaB and DnaC by steps that include ammonium sulfate precipitation, affinity column chromatography and gel filtration column chromatography.

DnaA was prepared by purifying an *E. coli* strain expressing DnaA by steps that include ammonium sulfate precipitation, dialysis precipitation, and gel filtration column chromatography.

GyrA and GyrB were prepared by purifying a mixture of an *E. coli* strain expressing GyrA and an *E. coli* strain expressing GyrB by steps that include ammonium sulfate precipitation, affinity column chromatography and gel filtration column chromatography.

Topo IV was prepared by purifying a mixture of an *E. coli* strain expressing ParC and an *E. coli* strain expressing ParE by steps that include ammonium sulfate precipitation, affinity column chromatography and gel filtration column chromatography.

Topo III was prepared by purifying an *E. coli* strain expressing Topo III by steps that include ammonium sulfate precipitation, and affinity column chromatography.

RecQ was prepared by purifying an *E. coli* strain expressing RecQ by steps that include ammonium sulfate precipitation, affinity column chromatography and gel filtration column chromatography.

Commercially available enzymes derived from *E. coli* were used for RNaseH, Ligase and PolI (Takara Bio Inc.).

As the template DNA, a 9.6 kb circular DNA (circular DNA having a replication origin sequence oriC, kanamycin resistance (Km)), a 80 kb long chain circular DNA (circular DNA having a replication origin sequence oriC, kanamycin resistance (Km)), a 200 kb long chain circular DNA (circular DNA having a replication origin sequence oriC, kanamycin resistance (Km)) or a DNA cyclized by in vitro ligation were used.

The 9.6 kb circular DNA and the 80 kb and 200 kb long chain circular DNAs were prepared by in vivo recombination in *E. coli* cells. Specifically, an in vivo recombination was performed using *E. coli* expressing a recombination protein group of λ phage to prepare circular DNA of a desired length including a kanamycin resistance cassette and a region in the *E. coli* chromosome that includes oriC.

Figure 2:
FIG. 2 shows the structure of DNA cyclized by in vitro ligation using the Gibson Assembly method.
Figure 2:

A method for preparing circular DNA by in vitro ligation is shown in FIG. 2.

Specifically, a PCR fragment (2.3 kb) having a replication origin sequence oriC and a region having kanamycin resistance (Km) was ligated with a PCR fragment having sequences of the dnaA gene and dnaN gene (hereinafter referred to as dnaA-dnaN fragment) (2.6 kb) by a reaction using the Gibson assembly method. The two PCR fragments were ligated through homologous sequences of 20 bases (referred to as H1, H2) attached to both ends to form a circular structure. The reaction was performed by mixing the above two PCR fragments with the Gibson Assembly Master Mix (NEB) and letting the mixture react at 50° C. for 15 min. After the reaction, 0.1 microliter of the reaction solution (1 microliter of the reaction solution diluted to 10 folds) was used as the template DNA to be added directly to an amplification reaction system of 10 microliters (constitution of Table 1), and the mixture was reacted at 30° C. for 1 h.

Figure 3:
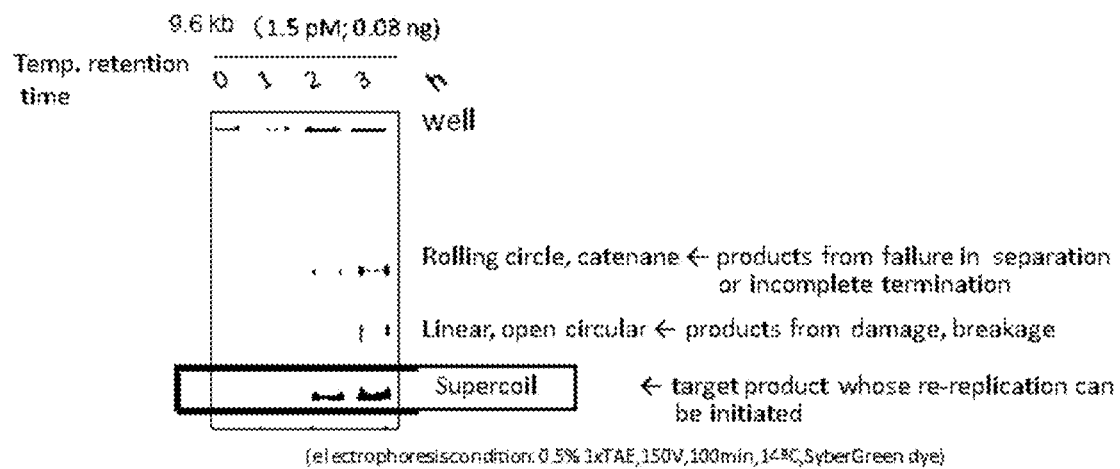
FIG. 3 shows the detection result of the amplification product at each reaction time in a case in which a circular DNA of 9.6 kb was used as a template, the detection result obtained by using SYBR Green after subjecting the product to agarose electrophoresis.

<Result 1> Case Using 9.6 kb Circular DNA (0.08 ng, about $10^7$ of Circular Molecules) as Template FIG. 3 shows the detection result of the amplification product using SYBR Green.

The circular DNA amplification product having a supercoil structure (indicated by a black box) was confirmed as well as a byproduct (a reaction intermediate).

The amplification amount of circular DNA was obtained by transforming an *E. coli* DH5a strain using the solution after reaction as it was, cultivating the strain in a kanamycin-containing agar, and measuring the number of colonies, and the result is shown in Table 2. A reaction solution whose temperature had been retained for 0 h. was used as the control.

TABLE 2

| Temperature Retention Time | 0 hour | 3 hours |
|---|---|---|
| Transformation Product (Number of colonies) | 9 | $5.4 \times 10^4$ |

The method of the present invention enabled a 9.6 kb circular DNA to be amplified to 6,000 folds of circular DNA.

Figure 4:
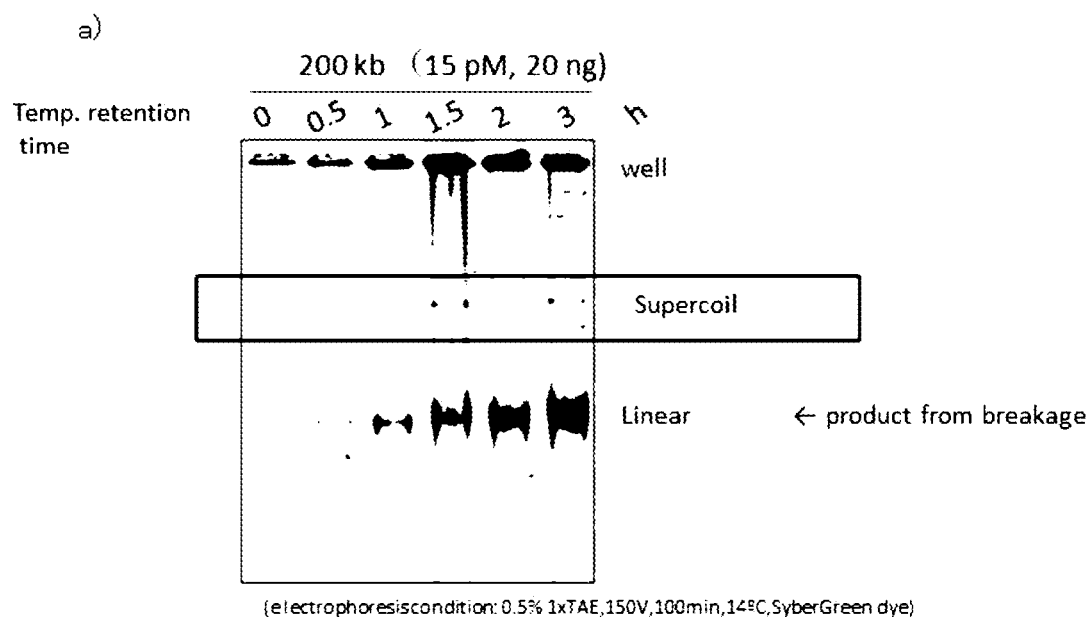
FIG. 4 shows the detection results of the amplification products in a case in which long chain circular DNAs of 200 kb and 80 kb were used as templates, the detection result obtained by using SYBR Green after subjecting the product to agarose electrophoresis.
Figure 4:
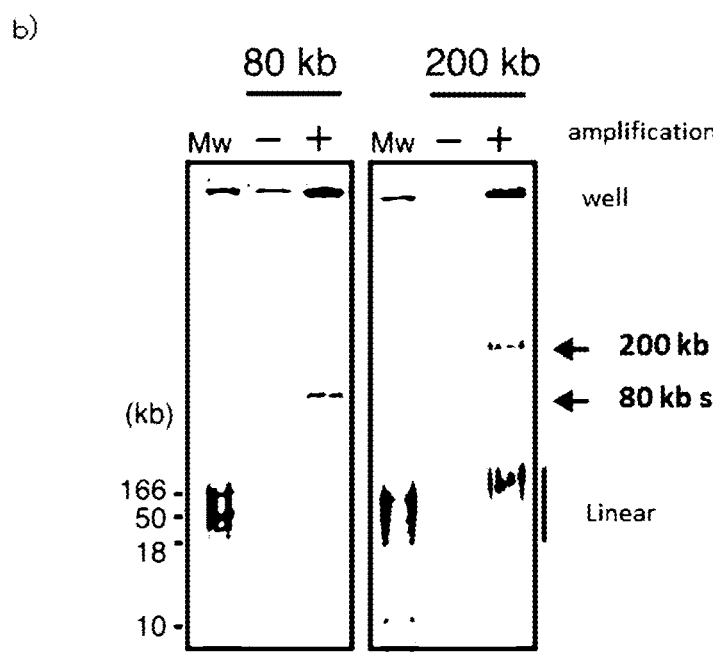

<Result 2> Case Using 80 kb and 200 kb Long Chain Circular DNAs as Templates FIG. 4 shows the detection result of an amplification product obtained using SYBR Green.

The circular DNA amplification product having a supercoil structure (indicated by a black box or arrow) was confirmed.

The method of the present invention showed that a good amplification product may be obtained even when long circular DNAs of 80 kb or 200 kb are used as templates.

Figure 5:
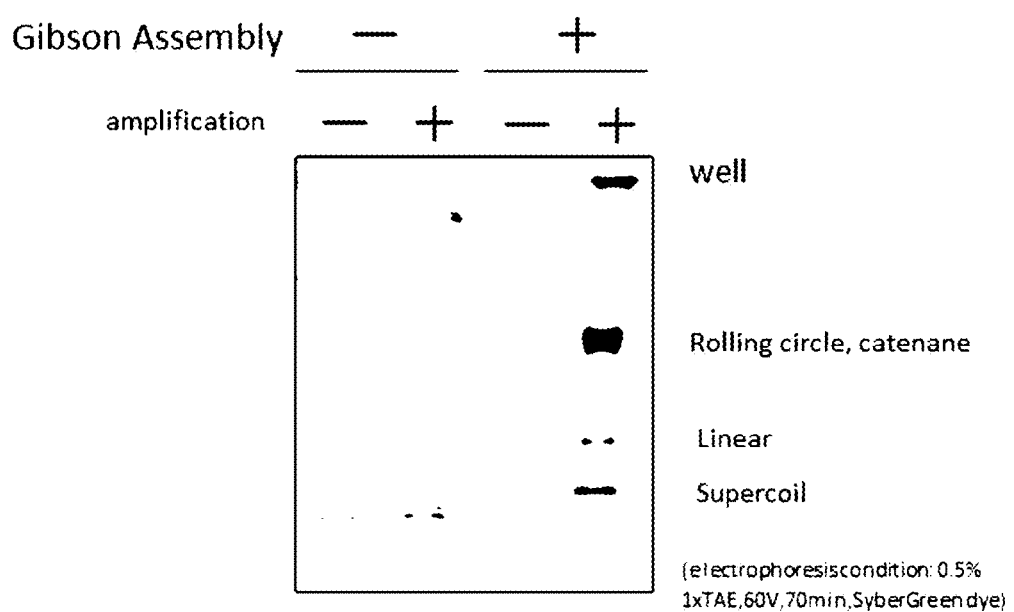
FIG. 5 shows the detection result of the amplification product in a case in which DNA cyclized by in vitro ligation using the Gibson Assembly method was used as a template, the detection result obtained by using SYBR Green after subjecting the product to agarose electrophoresis.

<Result 3> Case Using DNA Cyclized by In Vitro Ligation as Template FIG. 5 shows the detection result of an amplification product detected by using SYBR Green.

The method of the present invention showed that a good amplification product may be obtained even when DNA cyclized by in vitro ligation is used as the template.

The amplification amount of circular DNA was obtained by transforming an *E. coli* DH5a strain using the solution after reaction as it was, cultivating the strain in a kanamycin-containing agar, and measuring the number of colonies, and its result is shown in Table 3. A sample that was not subjected to amplification was used as the control.

TABLE 3

| Amplification Reaction | − | + |
|---|---|---|
| Transformation Product (Number of colonies) | $3.2 \times 10^2$ | $6.6 \times 10^5$ |

The method of the present invention enabled the DNA cyclized by using the Gibson Assembly method to be amplified to 2,000 folds in circular DNA.

Example 2: Amplification of Circular DNA from Few Template Molecules

The 9.6 kb circular DNA shown in Example 1 was used to perform amplification similar to Example 1.

(2-1) Analysis of Amplification Efficiency

Figure 6:
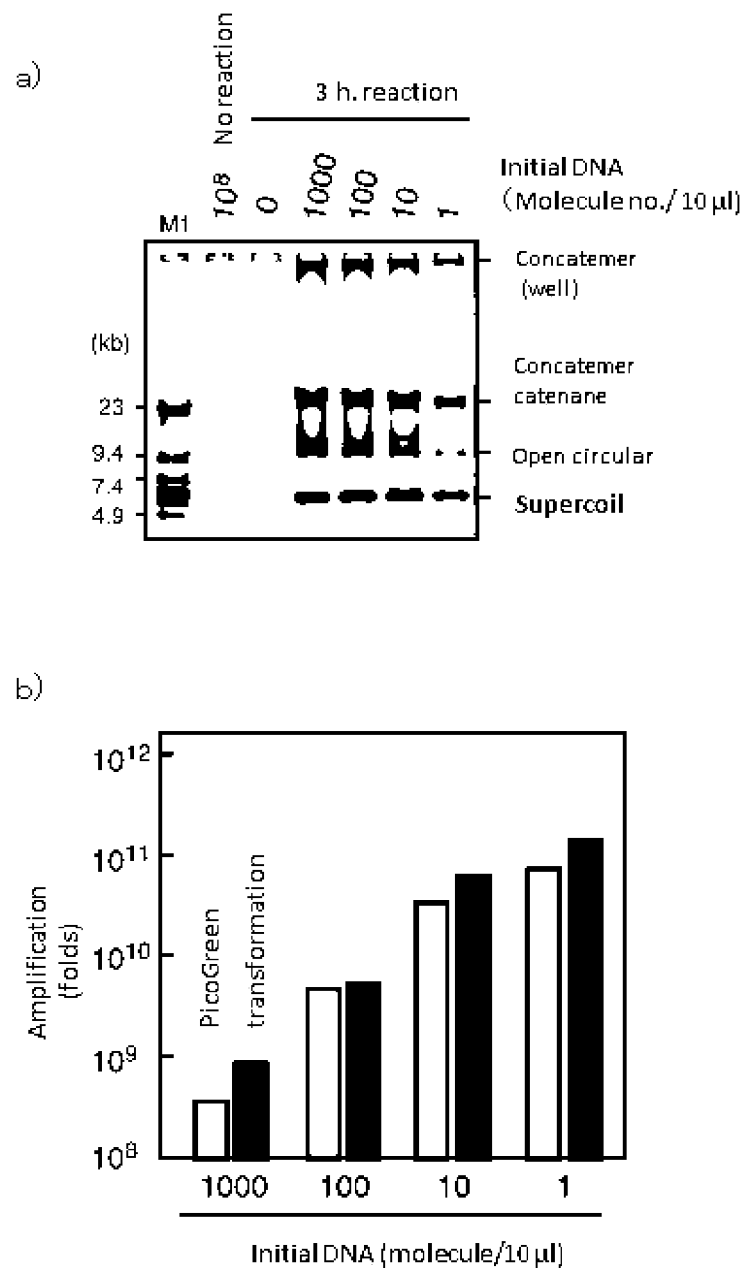
FIG. 6 shows the result of the amplification experiment in which a circular DNA of 9.6 kb in a minute amount (at a level of one molecule) was used as a template.

To 10 μl of an amplification reaction solution (Example 1, Table 2) was added a 9.6 kb circular DNA so that the solution contained 1 to 1,000 circular molecules, then the temperature of the solution was retained at 30° C. for 3 h. to let amplification progress. The reaction product was subjected to 0.5% agarose electrophoresis and stained with SybrGreen (Takara Bio Inc.) to detect amplified DNA (FIG. 6a). Furthermore, the total amount of DNA of the amplification product was quantified by using the PicoGreen Detection kit (ThermoFisher) (FIG. 6b: PicoGreen Method). The amplification amount of the circular DNA molecule was quantified by directly transforming the amplification product to *E. coli*, and calculating the number of kanamycin resistance colonies (FIG. 6b: Transformation). The quantification result was used to obtain the level of amplification against the initial DNA amount (amplification), and the result is shown in the graph.

The above result made evident that a single molecule of circular DNA constituting the template DNA may be amplified to about 1011 molecules by a mere 3 h. of isothermal reaction (amplification of about 100 billion folds).

(2-2) Analysis of Doubling Time

Figure 7:
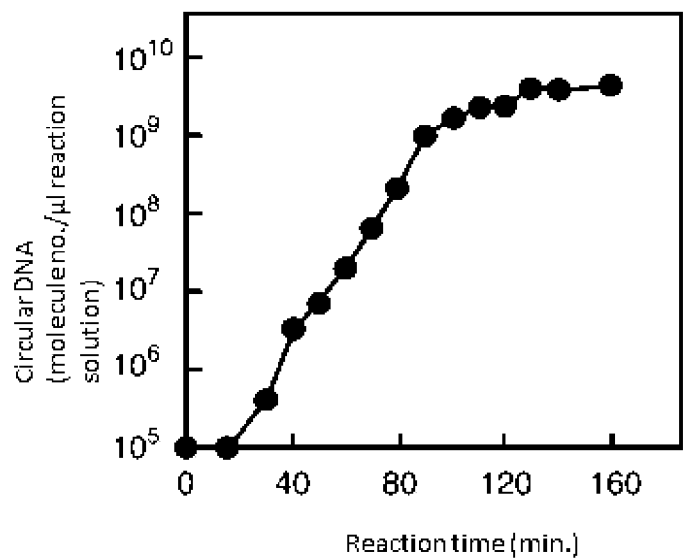
FIG. 7 is a graph that depicts the number of amplified circular DNA molecules corresponding to the amplification time in a case in which a circular DNA of 9.6 kb was used as a template.

To 80 μl of amplification reaction solution (Example 1, Table 1), the above circular DNA was added and the temperature of the solution was retained at 30° C. to let amplification progress. Circular DNA was added so that every 1 μl of the reaction solution contained 105 molecules. The number of amplified circular DNA was quantified by sampling the solution over time, directly transforming the sample to *E. coli*, and calculating the number of kanamycin resistance colonies (FIG. 7).

It was confirmed from the above result that the doubling time of 9.6 kb circular DNA molecules is about 5 min.

Example 3: Amplification of Single, Circular DNA Clone from Mixture

Amplification of a single, circular DNA clone was performed from a mixture of a 9.6 kb circular DNA and a 12.0 kb circular DNA shown in Example 1 (circular DNA having a replication origin sequence oriC, kanamycin resistance (Km)).

The 12.0 kb circular DNA was prepared by in vivo recombination in *E. coli* cells. Specifically, in vivo recombination was performed using *E. coli* expressing a recombination protein group of λ phage to prepare circular DNA of a desired length including oriC and a cassette consisting of a kanamycin resistance gene and some region in the *E. coli* chromosome.

Figure 8:
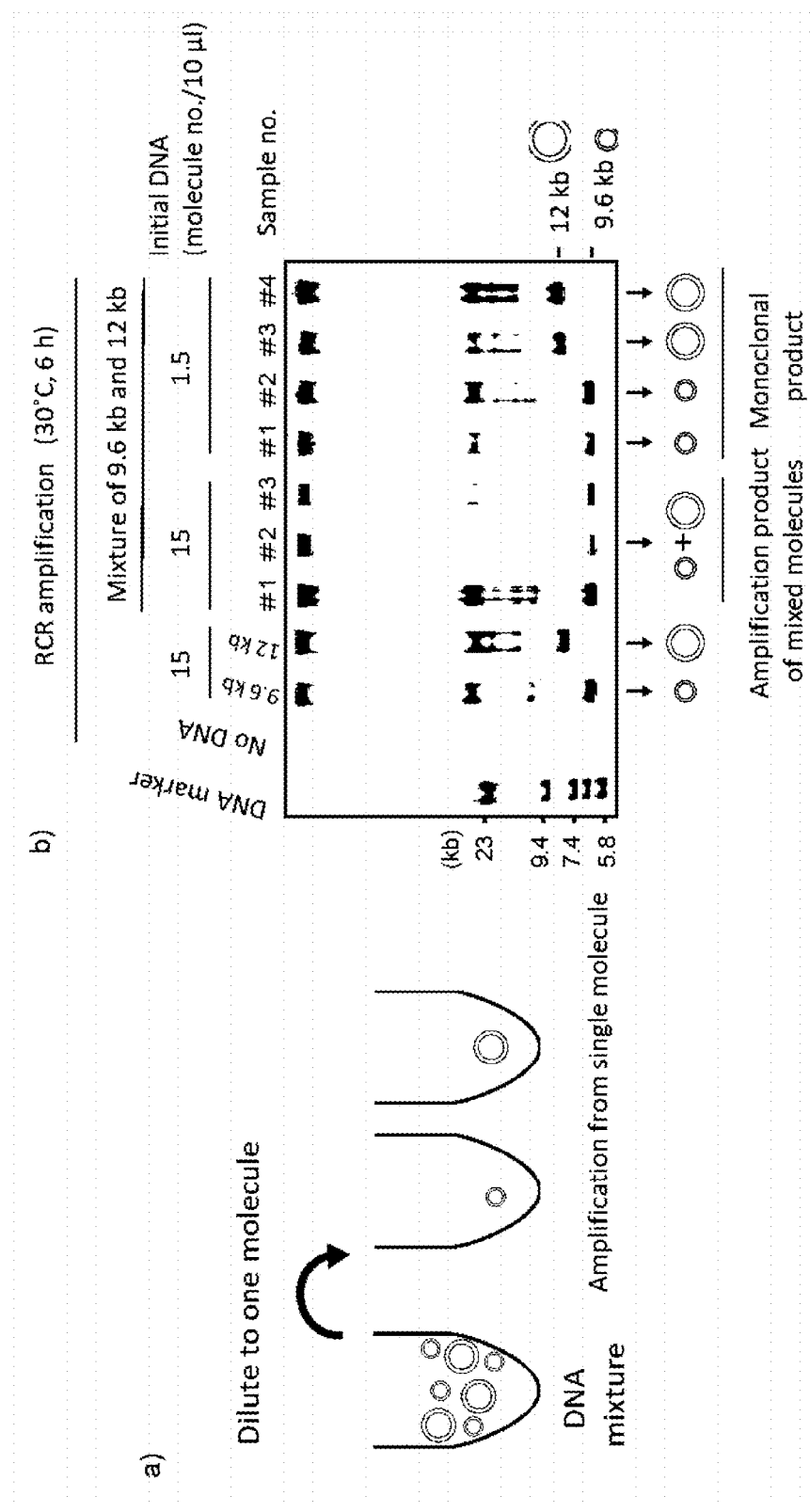
FIG. 8 is a diagram showing the amplification test result of a single circular DNA clone in a mixture.

To 10 μl of the amplification reaction solution (Example 1, Table 1), a mixture of the above two types of circular DNAs was added so that the reaction solution would contain each type of circular DNA in a number of 15 molecules or diluted to 1.5 molecules, then the temperature was retained at 30° C. for 6 h. to let amplification progress. From the reaction product, the amplification DNA was detected by subjecting the product to 0.5% agarose electrophoresis and staining it with SybrGreen (Takara Bio Inc.) (FIG. 8).

As a result, the clone of just one of the two types of circular DNAs was amplified for each of all reaction samples in the reaction solution diluted to 1.5 molecules of circular DNA. This shows that, even if the template DNA is a mixture, it is possible to amplify a single, circular DNA clone by diluting the mixture to a level of 1 molecule in the reaction solution.

Example 4: Passage Amplification

The passage amplification of circular DNA was tested using lacZ circular DNA.

Figure 9:
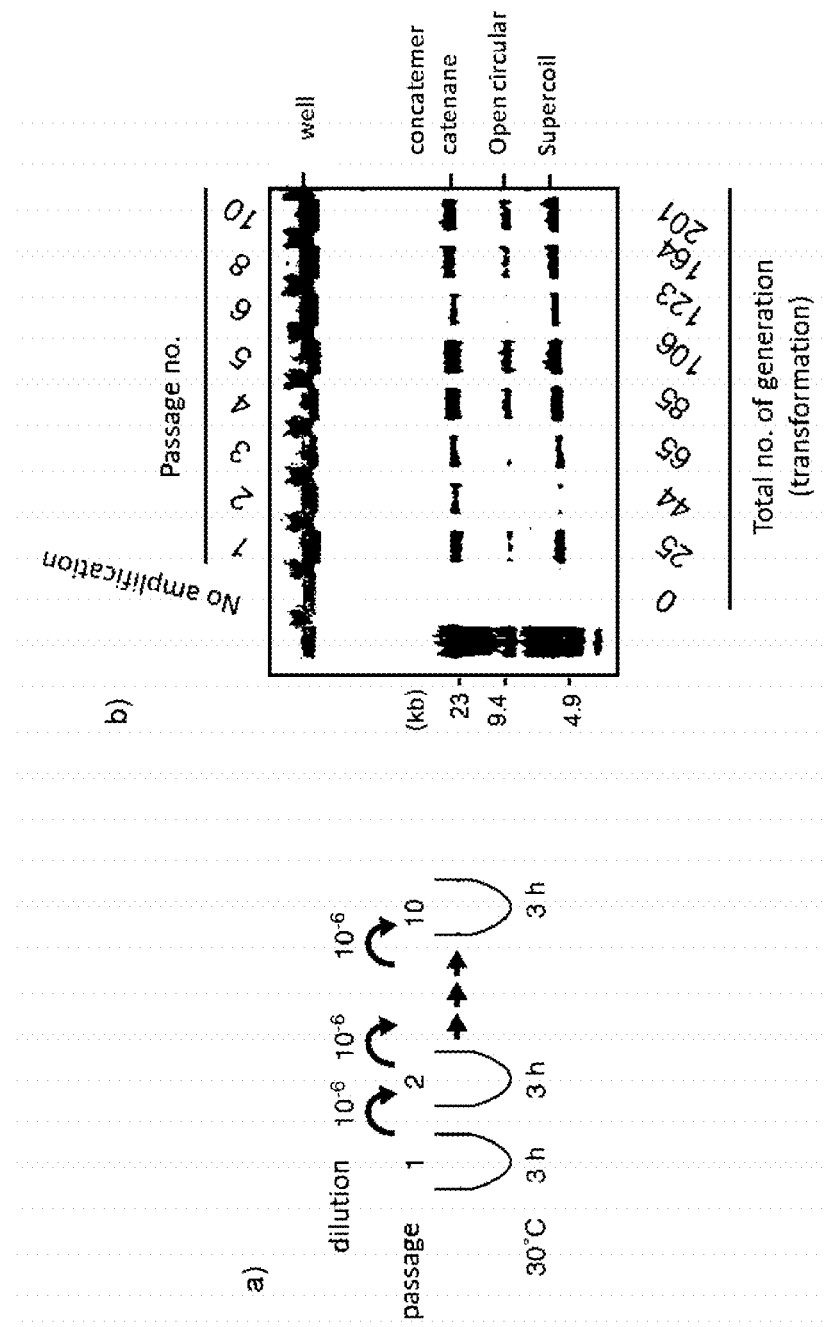
FIG. 9 is a diagram showing the passage amplification test result of circular DNA.

The lacZ circular DNA (9.0 kb) was prepared by ligating a double strand DNA fragment including oriC (1.0 kb), a double strand DNA fragment including kanamycin resistance gene (Km) (4.6 kb) and a double strand DNA fragment including lacZ (β-galactosidase) gene (3.4 kb). To 10 µl of amplification reaction solution (Example 1, Table 1) was added lacZ circular DNA so that the solution contains 1,000 molecules of the DNA, then the temperature of the solution was retained at 30° C. for 3 h. to let amplification progress. This constitutes one passage. The amplification reaction product from the previous passage number was diluted to 105 folds, and 1 µl of this was added to the new amplification reaction solution to induce a similar reaction to constitute the next passage amplification. The passage amplification was repeated 10 times. The amplification product of each passage was detected by being subjected to 0.5% agarose electrophoresis and stained with SybrGreen (Takara Bio Inc.) (FIG. 9). A part of the amplification product was transformed to $E.$ $coli$ and the level of DNA amplification was quantified by the number of kanamycin resistance colonies, then this number was used to calculate the number of generations the exponential amplification was repeated which constitutes the total number of generations.

It was consequently recognized that the amplification of circular DNA was progressing efficiently even after 10 passages. As the result of Example 2 (FIG. 7) shows, when the circular DNA amplifies to a certain extent, the amplification rate levels off due to the exhaustion of the substrate or enzyme. Meanwhile, the result of the present Example shows that it is possible to semipermanently repeat an exponential amplification of circular DNA by passaging a part of the amplification reaction product in the new reaction solution. In other words, the method of the present invention is a method which enables amplification of circular DNA to be performed similarly to the passage amplification of cells.

Example 5: Incidence of Replication Error in Amplification

Because the template circular DNA in Example 4 includes lacZ genes, the colony that expresses lacZ genes properly (lacZ$^+$) becomes blue since it can decompose X-gal and the colony whose lacZ gene does not function properly due to mutation introduced by an error in replication (lacZ$^-$) becomes white since it cannot decompose X-gal when $E.$ $coli$ that had been transformed by the above circular genes is cultivated in the X-gal plate. In other words, it is possible to judge the replication error in the amplified circular DNA by the color that the $E.$ $coli$ that had been transformed by the aforementioned circular genes expresses in the X-gal plate.

The amplification reaction product of each passage sample was directly transformed to $E.$ $coli$, and cultivated on the X-gal plate to obtain the lacZ$^-$ incidence. The lacZ$^-$ incidence and the total number of generation obtained in Example 4 were used to calculate the error incidence of one generation of replication cycle according to the method of Barnes (Barnes W M Gene. 1992, 112, 29-35). The result is shown in Table 4 below.

TABLE 4

| Passage Number | Total Number of Generations | lacZ$^-$ colony incidences (%) | Error incidence (per base) |
|---|---|---|---|
| 1 | 25 | <0.045 | <3.7 × 10$^{-8}$ |
| 2 | 44 | <0.074 | <3.4 × 10$^{-8}$ |
| 5 | 106 | 0.1 | 1.9 × 10$^{-8}$ |
| 10 | 201 | 0.093 | 0.93 × 10$^{-8}$ |

The above result shows that replication errors occur at approximately one position per 100 million bases (an average of $1.4 \times 10^{-8}$ errors per base). This is about the same as the mutation rate in the cell (strains without mismatch correction system), and about 10 thousand times more accurate than Taq polymerase.

Example 6: Addition of Exonuclease and RecG

The effects obtained in a case where the 80 kb circular DNA described in Example 1 was used, and RecG-type helicase and linear DNA-specific exonuclease were further added to the amplification reaction solution to carry out an amplification reaction, were studied.

The 80 kb circular DNA was prepared as described in Example 1.

RecG was used as RecG-type helicase. RecG was prepared by being purified from a RecG expressing $Escherichia$ $coli$ strain in a step involving ammonium sulfate precipitation and affinity column chromatography.

As linear DNA-specific exonuclease, Plasmid-Safe™ ATP-Dependent DNase (epicentre), which is commercially available exonuclease, was used. The number of units was set according to the instructions of the manufacturer.

An amplification reaction solution (10 µl) was prepared by adding the 80 kb circular DNA (0.8 µg/µl or 8 µg/µl), RecG (0 nM, 100 nM, 300 nM, or 1000 nM), and linear DNA-specific exonuclease (0 U/µl or 0.2 U/µl), to the reaction composition shown in Table 1 of Example 1. An amplification reaction was carried out by retaining the thus prepared amplification reaction solution (10 µl) at 30° C. for 24 hours. The reaction product was subjected to 0.5% agarose gel electrophoresis (1×TAE buffer, 150 V, 100 minutes), and was then stained with SybrGreen (Takara Bio, Inc.) to detect the amplified DNA.

Figure 10:
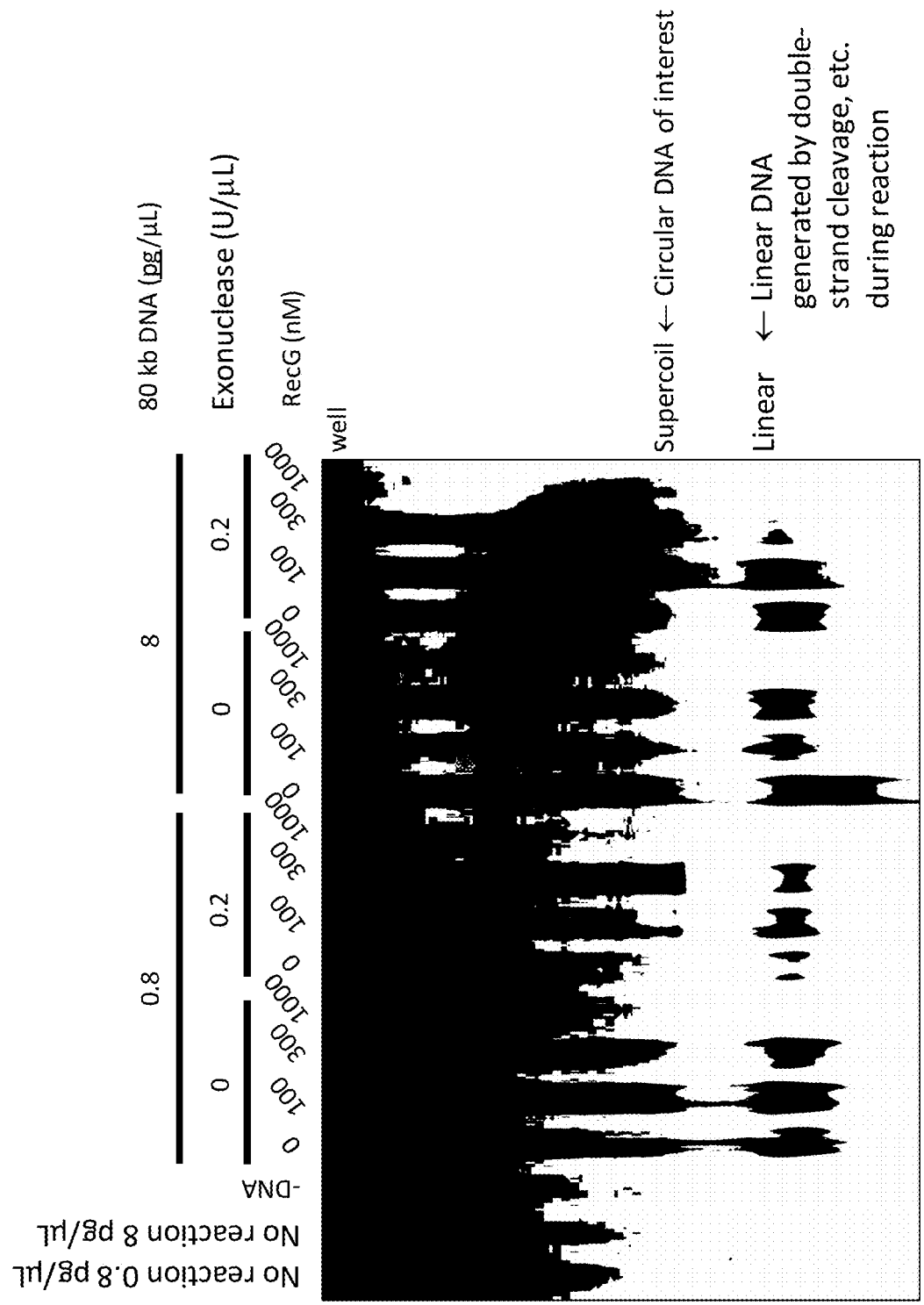
FIG. 10 shows the results obtained by subjecting an amplification product, which has been obtained by using 80 kb circular DNA as a template and adding RecG and linear DNA-specific exonuclease thereto, to agarose gel electrophoresis, and then detecting it by SYBR Green.

As a result, generation of linear DNA as a by-product caused by the cleavage of DNA, etc., was reduced by addition of RecG and linear DNA-specific exonuclease, and the improvement of the amount of the generated circular DNA amplification product having a supercoiled structure of interest was observed (FIG. 10).

Example 7: Studies of Various Types of Conditions

The results obtained by studying conditions for individual components contained in the reaction solution are shown.
1. Methods
As circular DNA as a template, 8.0 kb circular DNA was used. The 8.0 kb circular DNA was produced by inserting an oriC fragment into an M13mp18 plasmid vector.

Regarding Conditions A to R, the 8.0 kb circular DNA was added to the amplification reaction solution shown in Table 5 to a final concentration of 8.0 ng/µl or 0.8 ng/µl, and the obtained mixture was then reacted at 30° C. for 1 hour. [α-$^{32}$P]dATP had previously been added to the reaction solution, and after completion of the DNA replication reaction, the amount of dNTP incorporated into the template DNA was measured using a liquid scintillation counter. With regard to the amount of the incorporated dNTP, the value for 25 µl of the reaction solution was calculated. Using circular DNA having a final concentration of 8.0 ng/µl as a template, when 100% of the replication reaction has progressed (one round of replication), 600 pmol dNTP is incorporated into the template DNA. After an aliquot of the reaction solution had been subjected to agarose gel electrophoresis, a $^{32}$P incorporated product was detected with BAS Imaging Plate, thereby confirming generation of a supercoiled structure of interest.

Regarding Condition S, the 8.0 kb circular DNA was added to the amplification reaction solution shown in Table 5 to a final concentration of 8.0 ng/µl or 0.8 ng/µl, and the obtained mixture was then reacted at 30° C. for 2 hours. The reaction product was subjected to 0.5% agarose gel electrophoresis (1×TAE buffer, 150 V, 100 minutes), and was then stained with SybrGreen (Takara Bio, Inc.) to detect the amplified DNA.

TABLE 5

| | Condition (FIG.) | | | | | | | |
|---|---|---|---|---|---|---|---|---|
| | A (FIG. 11) | B (FIG. 12) | C (FIG. 13) | D (FIG. 14) | E (FIG. 15) | F (FIG. 16) | G (FIG. 17) | H (FIG. 18) |
| Tris-HCl (.0) | 20 mM | 20 mM | 20 mM | 20 mM | 20 mM | 20 mM | 20 mM | 20 mM |
| DTT | 8 mM | 8 mM | 8 mM | 8 mM | 8 mM | 8 mM | 8 mM | 8 mM |
| K + Glu- | 50 mM | — | 50 mM | 50 mM | 50 mM | 50 mM | 50 mM | Indicated |
| Mg(oAc)2 | 10 mM | 10 mM | 10 mM | 10 mM | 10 mM | 10 mM | 10 mM | 10 mM |
| Creatine Phosphate | 4 mM | 4 mM | 4 mM | 4 mM | 4 mM | 4 mM | 4 mM | 4 mM |
| ATP | 1 mM | 1 mM | 1 mM | 1 mM | 1 mM | 1 mM | 1 mM | 1 mM |
| G, C, UTP | 0.2 mM each | 0.2 mM each | Indicated | 1 mM each | 1 mM each | 1 mM each | 1 mM each | 1 mM each |
| dNTPs | 0.1 mM | 0.1 mM | 0.1 mM | 0.1 mM | 0.1 mM | 0.1 mM | 0.1 mM | 0.1 mM |
| tRNA | — | — | — | — | — | — | — | — |
| NAD | 0.05 mM | 0.05 mM | 0.05 mM | 0.05 mM | 0.05 mM | 0.05 mM | 0.05 mM | 0.05 mM |
| Ammonium Sulfate | — | — | — | — | — | — | — | — |
| BSA | 0.1 mg/ml | 0.1 mg/ml | 0.1 mg/ml | 0.1 mg/ml | 0.1 mg/ml | 0.1 mg/ml | 0.1 mg/ml | 0.1 mg/ml |
| Creatin kinase | 20 ng/µl | 20 ng/µl | 20 ng/µl | 20 ng/µl | 20 ng/µl | 20 ng/µl | 20 ng/µl | 20 ng/µl |
| SSB | 300 nM | 200 nM | 200 nM | 200 nM | 200 nM | 200 nM | 200 nM | 200 nM |
| IHF | 80 nM | 80 nM | 80 nM | Indicated | 20 nM | 20 nM | 20 nM | 20 nM |
| DnaG | 400 nM | 200 nM | 400 nM | 200 nM | 200 nM | 200 nM | 200 nM | 200 nM |
| Clamp | 20 nM | 40 nM | 40 nM | 40 nM | 40 nM | 40 nM | 40 nM | 40 nM |
| PolIII* | 20 nM | 5 nM | 20 nM | 5 nM | 5 nM | 5 nM | 5 nM | 5 nM |
| DnaB-DnaC | 20 nM | 20 nM | 20 nM | 20 nM | 20 nM | 20 nM | Indicated | 20 nM |
| DnaA | 100 nM | 100 nM | 40 nM | 100 nM | 100 nM | 100 nM | 100 nM | 100 nM |
| RNaseH | 0.2 nM | 0.2 nM | 0.2 nM | 0.2 nM | 0.2 nM | 0.2 nM | 0.2 nM | 0.2 nM |
| Ligase | 20 nM | 20 nM | 20 nM | 20 nM | 20 nM | 20 nM | 20 nM | 20 nM |
| PolI | 20 nM | 20 nM | 20 nM | 20 nM | 20 nM | 20 nM | 20 nM | 20 nM |
| GyrA, GyrB | 80 nM | 150 nM | 150 nM | 25 nM | 25 nM | Indicated | 100 nM | 100 nM |
| Topo IV | 6.5 nM | 10 nM | 5 nM | 2 nM | 2 nM | 2 nM | 2 nM | 2 nM |
| Tupo III | — | — | — | — | — | — | — | — |
| RecQ | — | — | — | — | — | — | — | — |
| oriC circular DNA | 8 ng/µl (8 kb) | Indicated | 8 ng/µl (8 kb) | 8 ng/µl (8 kb) | 8 ng/µl (8 kb) | 8 ng/µl (8 kb) | 8 ng/µl (8 kb) | 8 ng/µl (8 kb) |

| | Condition (FIG.) | | | | | | | |
|---|---|---|---|---|---|---|---|---|
| | I (FIG. 19) | J (FIG. 20) | K (FIG. 21) | L (FIG. 22) | M (FIG. 23) | N (FIG. 24) | O (FIG. 25) | P (FIG. 26) |
| Tris-HCl (pH 8.0) | 20 mM | 20 mM | 20 mM | 20 mM | 20 mM | 20 mM | 20 mM | 20 mM |
| DTT | 8 mM | 8 mM | 8 mM | 8 mM | 8 mM | 8 mM | 8 mM | 8 mM |
| K + Glu- | 150 mM | 150 mM | 150 mM | 150 mM | 150 mM | 150 mM | 150 mM | 150 mM |
| Mg(oAc)2 | 10 mM | 10 mM | 10 mM | 10 mM | 10 mM | 10 mM | 10 mM | 10 mM |
| Creatine Phosphate | 4 mM | 4 mM | 4 mM | 4 mM | 4 mM | 4 mM | 4 mM | 4 mM |
| ATP | 1 mM | 1 mM | 1 mM | 1 mM | 1 mM | 1 mM | 1 mM | 1 mM |
| G, C, UTP | 1 mM each | 1 mM each | 1 mM each | 1 mM each | 1 mM each | 1 mM each | 1 mM each | 1 mM each |
| dNTPs | 0.1 mM | 0.1 mM | 0.1 mM | 0.1 mM | 0.1 mM | 0.1 mM | 0.1 mM | 0.1 mM each |
| tRNA | Indicated | 20 ng/µl | 20 ng/µl | 20 ng/µl | 20 ng/µl | 20 ng/µl | 20 ng/µl | 20 ng/µl |
| NAD | 0.05 mM | 0.05 mM | 0.05 mM | 0.05 mM | 0.05 mM | 0.05 mM | 0.05 mM | 0.05 mM |
| Ammonium Sulfate | — | — | — | — | — | — | — | — |
| BSA | 0.1 mg/ml + Indicated | 0.5 mg/ml | 0.5 mg/ml | 0.5 mg/ml | 0.5 mg/ml | 0.1 mg/ml | 0.1 mg/ml | 0.5 mg/ml |

TABLE 5-continued

| Component | | | | | | | |
|---|---|---|---|---|---|---|---|
| Creatin kinase | 20 ng/μl | 20 ng/μl | 20 ng/μl | 20 ng/μl | 20 ng/μl | 20 ng/μl | 20 ng/μl |
| SSB | 200 nM | 200 nM | Indicated | 200 nM | 50 nM | 50 nM | 100 nM |
| IHF | 20 nM | 20 nM | 20 nM | 20 nM | 20 nM | 20 nM | 20 nM |
| DnaG | 200 nM | 200 nM | 200 nM | 200 nM | 200 nM | 200 nM | 400 nM |
| Clamp | 40 nM | 40 nM | 40 nM | 40 nM | 40 nM | 40 nM | 40 nM |
| PolIII* | 5 nM | 5 nM | 5 nM | 5 nM | 3 nM | 5 nM | 5 nM |
| DnaB-DnaC | 20 nM | 20 nM | 20 nM | 20 nM | Indicated | 20 nM | 20 nM |
| DnaA | Indicated | 100 nM | 100 nM | 100 nM | 40 nM | 40 nM | 100 nM |
| RNaseH | 0.2 nM | 0.2 nM | 0.2 nM | 0.2 nM | 0.2 nM | Indicated | 10 nM |
| Ligase | 20 nM | Indicated | 20 nM | 20 nM | 50 nM | 50 nM | 50 nM |
| PolI | 20 nM | 20 nM | Indicated | 20 nM | 50 nM | 50 nM | 50 nM |
| GyrA, GyrB | 150 nM | 150 nM | 150 nM | 150 nM | 150 nM | 150 nM | 150 nM |
| Topo IV | 5 nM | 5 nM | 5 nM | 5 nM | 5 nM | 5 nM | 5 nM |
| Topo III | — | — | — | — | — | — | — |
| RecQ | 2 nM | — | — | — | — | — | — |
| oriC circular DNA | 0.8 ng/μl (8 kb) | 0.8 ng/μl (8 kb) | 0.8 ng/μl (8 kb) | 0.8 ng/μl (8 kb) | 0.8 ng/μl (8 kb) | 0.8 ng/μl (8 kb) | 0.8 ng/μl (8 kb) |

| Component | Condition (FIG.) | | |
|---|---|---|---|
| | Q (FIG. 27) | R (FIG. 28) | S (FIG. 29) |
| Tris-HCl (pH 8.0) | 20 mM | 20 mM | 20 mM |
| DTT | 8 mM | 8 mM | 8 mM |
| K + Glu- | 150 mM | 150 mM | 150 mM |
| Mg(oAc)2 | 10 mM | 10 mM | 10 mM |
| Creatine Phosphate | 4 mM | 4 mM | 4 mM |
| ATP | 1 mM | 1 mM | 1 mM |
| G, C, UTP | 1 mM each | 1 mM each | 1 mM each |
| dNTPs | 0.1 mM each | 0.1 mM each | 0.1 mM each |
| tRNA | 20 ng/μl | 20 ng/μl | 20 ng/μl + Indicated |
| NAD | 0.05 mM | 0.05 mM | 0.05 mM + Indicated |
| Ammonium Sulfate | — | — | Indicated |
| BSA | 0.5 mg/ml | 0.5 mg/ml | 0.5 mg/ml |
| Creatin kinase | 20 ng/μl | 20 ng/μl | 20 ng/μl |
| SSB | 100 nM | 100 nM | 100 nM + Indicated |
| IHF | 20 nM | 20 nM | 20 mM + Indicated |
| DnaG | 400 nM | 400 nM | 400 nM |
| Clamp | 40 nM | 40 nM | 40 nM |
| PolIII* | 5 nM | 5 nM | 5 nM |
| DnaB-DnaC | 20 nM | 20 nM | 20 nM |
| DnaA | 100 nM | 100 nM | 100 nM |
| RNaseH | 10 nM | 10 nM | 10 nM |
| Ligase | 50 nM | 50 nM | 50 nM |
| PolI | 50 nM | 50 nM | 50 nM |
| GyrA, GyrB | 150 nM | 50 nM | 50 nM |
| Top IV | Indicated | 0 nM | 0 nM/Indicated |
| Topo III | Indicated | 50 nM | 50 nM |
| RecQ | — | 50 nM | 50 nM |
| oriC circular DNA | 0.8 ng/μl (8 kb) | 0.8 ng/μl (8 kb) | 8 ng/μl (8 kb) |

2. Results
(1) Condition A

Figure 11:
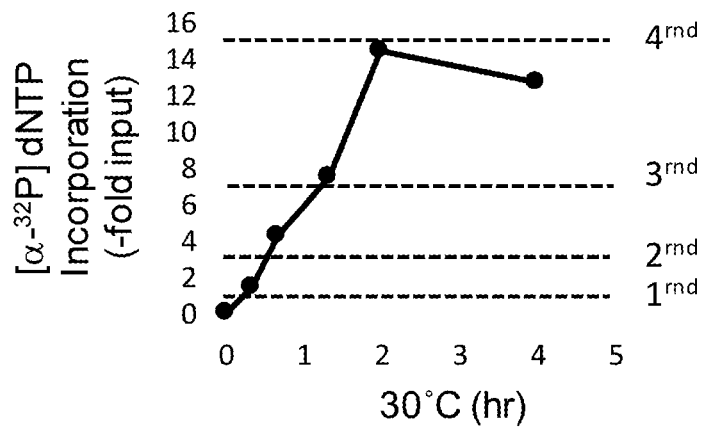
FIG. 11 is a graph showing the results of Condition A in Example 7.

It was found that several rounds of replication cycles can be repeatedly carried out by adding the first, second and third enzyme groups to the reaction system and performing a reaction. However, it was also found that, since substrate proteins used in the reaction are reduced as replication cycles are repeated, the replication cycles are stagnated at the 4th round (FIG. 11).

(2) Condition B

Whether or not the number of replication cycles can be improved by reducing the amount of template DNA at the time of initiation of the reaction was studied. The amount of template DNA at the time of initiation of the reaction was set at 8 ng/µl and 0.8 ng/µl, and it was then studied.

Figure 12:
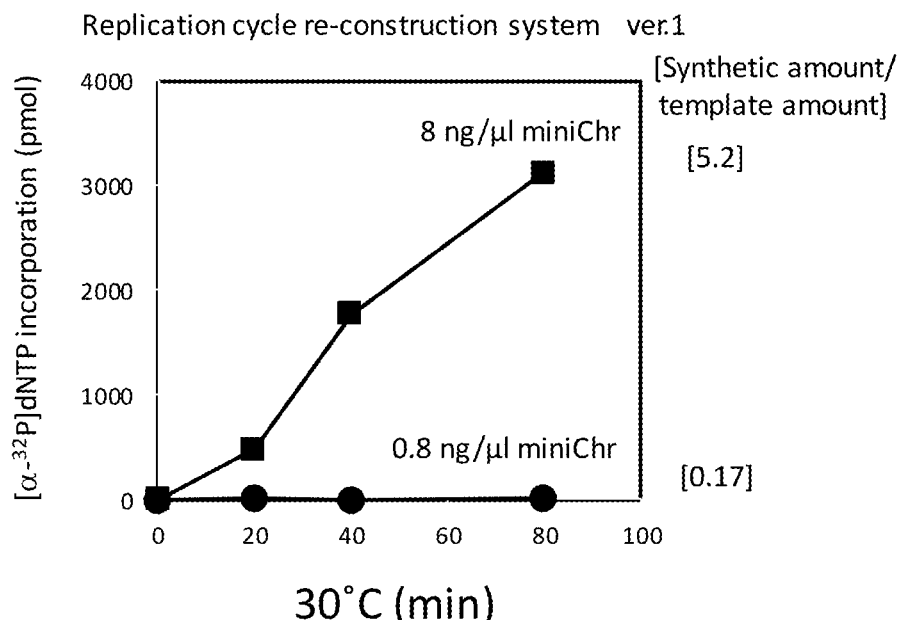
FIG. 12 is a graph showing the results of Condition B in Example 7.

As a result, when the amount of template DNA at the time of initiation of the reaction was 8 ng/µl, the replication reaction was observed, but when the amount of template DNA was reduced to 0.8 ng/µl, the replication efficiency was significantly inhibited, and amplification of DNA was not observed (FIG. 12). These results demonstrate that, in order to improve the number of replication cycles, a reduction in the amount of template DNA may not only be needed, but conditions including the amounts of various types of components in the reaction composition may also need to be studied.

(3) Condition C

The amounts of GTP, CTP and UTP in the reaction composition were studied. The concentration of GTP, CTP and UTP at the initiation of the reaction was set at 0.2 mM, 0.5 mM, 1.0 mM and 2.0 mM.

Figure 13:
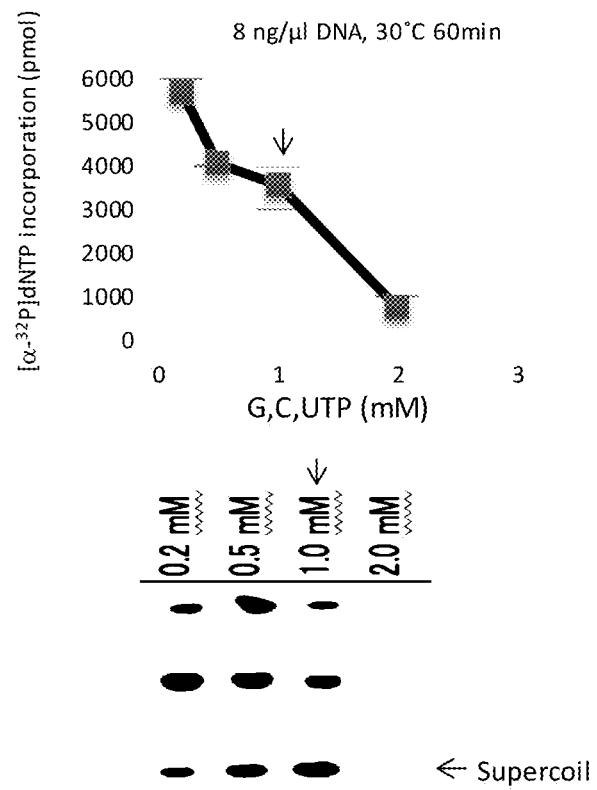
FIG. 13 is a graph showing the results of Condition C (studies regarding the amounts of GTP, CTP and UTP) and a gel electrophoretic photograph in Example 7.

The results are shown in FIG. 13.

(4) Condition D

The amount of IHF in the reaction composition was studied. The concentration of IHF at the initiation of the reaction was set at 0 nM, 10 nM, 20 nM, 40 nM, 100 nM, and 200 nM.

Figure 14:
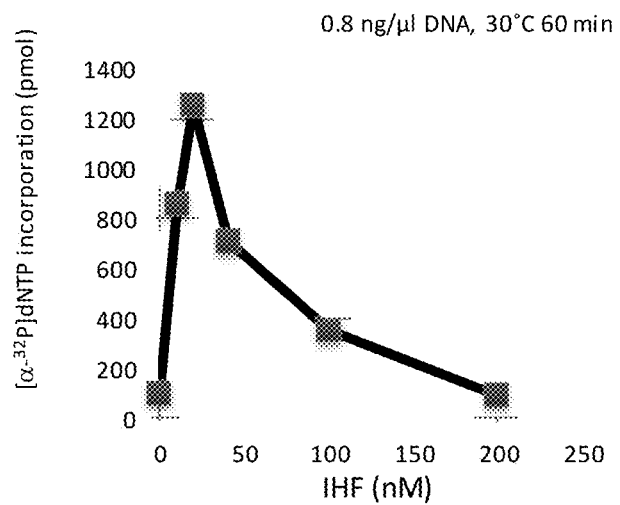
FIG. 14 is a graph showing the results of Condition D (studies regarding the amount of IHF) in Example 7.

The results are shown in FIG. 14.

(5) Condition E

The amount of Topo IV in the reaction composition was studied. The concentration of Topo IV at the initiation of the reaction was set at 0 nM, 1 nM, 2 nM, 5 nM, 10 nM, and 20 nM.

Figure 15:
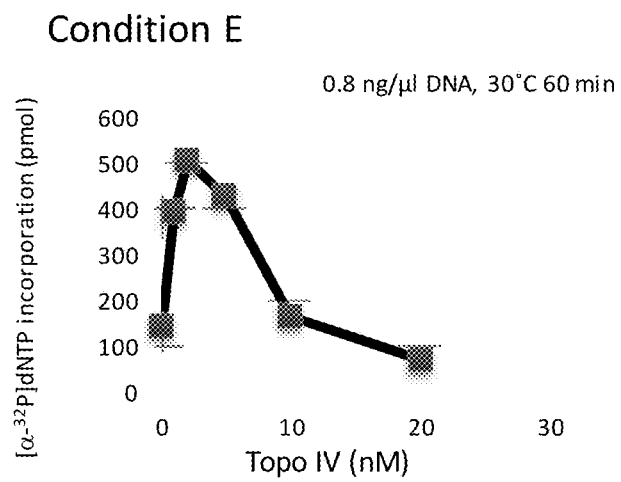
FIG. 15 is a graph showing the results of Condition E (studies regarding the amount of Topo IV) in Example 7.

The results are shown in FIG. 15.

(6) Condition F

The amount of DNA gyrase in the reaction composition was studied. The concentration of a GyrA-GyrB complex at the initiation of the reaction was set at 0 nM, 10 nM, 25 nM, 50 nM, 100 nM, and 200 nM.

Figure 16:
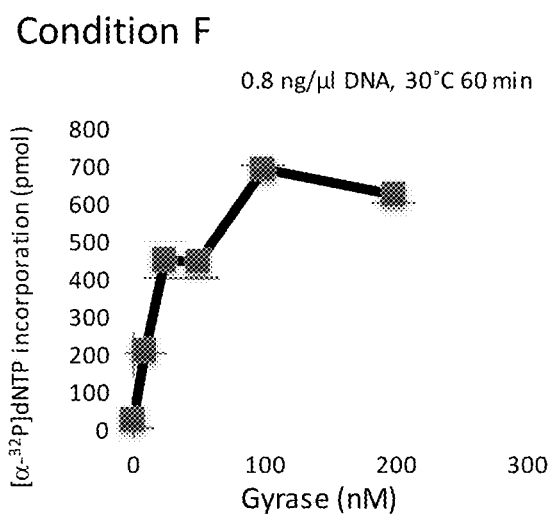
FIG. 16 is a graph showing the results of Condition F (studies regarding the amount of DNA gyrase) in Example 7.

The results are shown in FIG. 16.

(7) Condition G

The amount of DNA polymerase III* in the reaction composition was studied. The concentration of Pol III* at the initiation of the reaction was set at 0 nM, 1 nM, 2 nM, 5 nM, and 10 nM.

Figure 17:
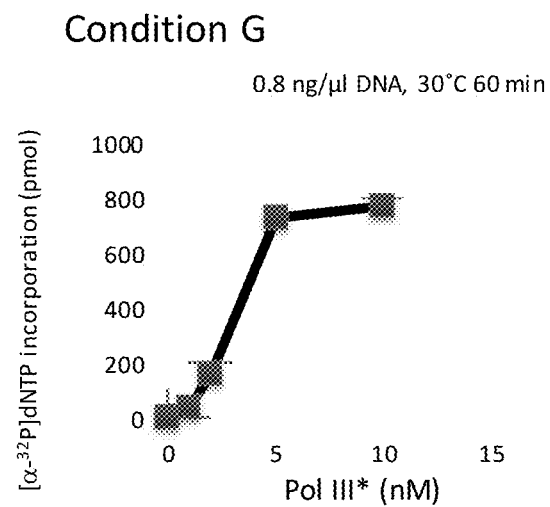
FIG. 17 is a graph showing the results of Condition G (studies regarding the amount of DNA polymerase III*) in Example 7.

The results are shown in FIG. 17.

(8) Condition H

The amount of an alkali metal ion source in the reaction composition was studied. The concentration of potassium glutamate at the initiation of the reaction was set at 50 mM and 150 mM.

Figure 18:
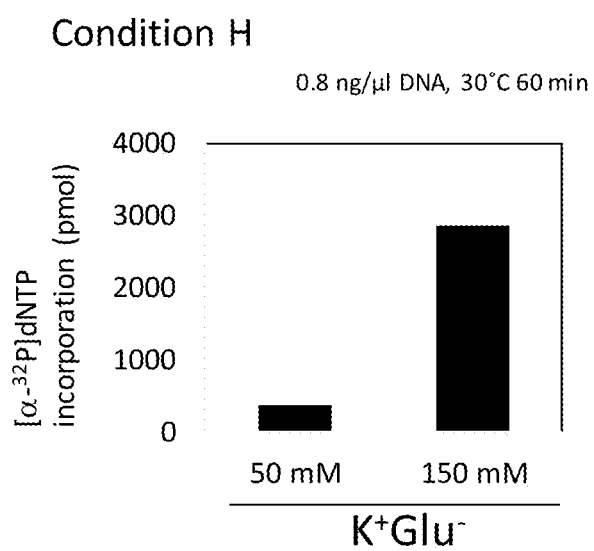
FIG. 18 is a graph showing the results of Condition H (studies regarding the amount of an alkali metal ion source) in Example 7.

The results are shown in FIG. 18.

(9) Condition I

The amounts of a protein non-specific adsorption inhibitor and/or a nucleic acid non-specific adsorption inhibitor in the reaction composition were studied. Conditions in which tRNA is not contained but 0.1 mg/ml BSA is contained in the reaction composition; conditions in which 20 ng/µl tRNA and 0.1 mg/ml BSA are contained in the reaction composition; and conditions in which tRNA is not contained but 0.5 mg/ml BSA is contained in the reaction composition, were studied.

Figure 19:
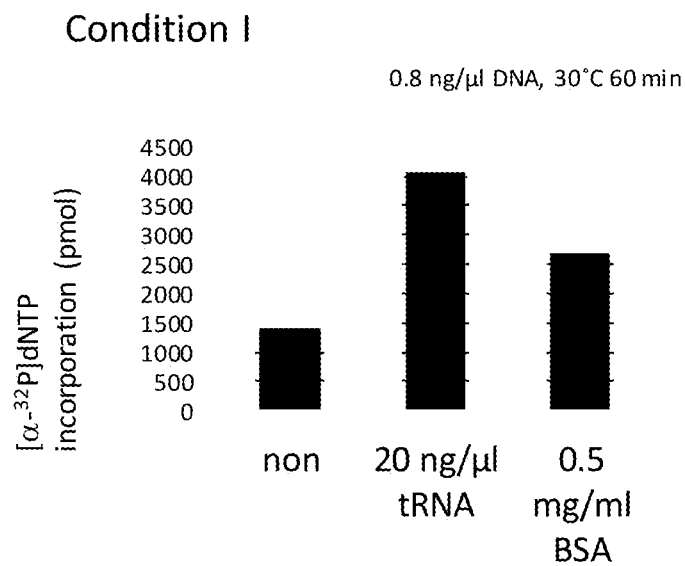
FIG. 19 is a graph showing the results of Condition I (studies regarding the amounts of a protein non-specific adsorption inhibitor and/or a nucleic acid non-specific adsorption inhibitor) in Example 7.

The results are shown in FIG. 19.

(10) Condition J

The amount of an enzyme having DnaA activity in the reaction composition was studied. The concentration of DnaA at the initiation of the reaction was set at 0 nM, 5 nM, 10 nM, 20 nM, 40 nM, 100 nM, and 200 nM.

Figure 20:
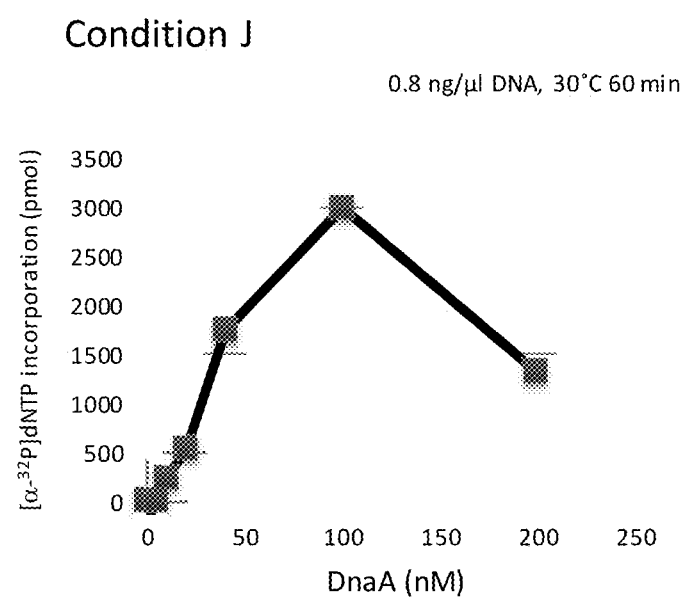
FIG. 20 is a graph showing the results of Condition J (studies regarding the amount of an enzyme having DnaA activity) in Example 7.

The results are shown in FIG. 20.

(11) Condition K

The amount of an enzyme having DNA ligase activity in the reaction composition was studied. The concentration of ligase at the initiation of the reaction was set at 0 nM, 2 nM, 5 nM, 10 nM, 20 nM, and 50 nM.

Figure 21:
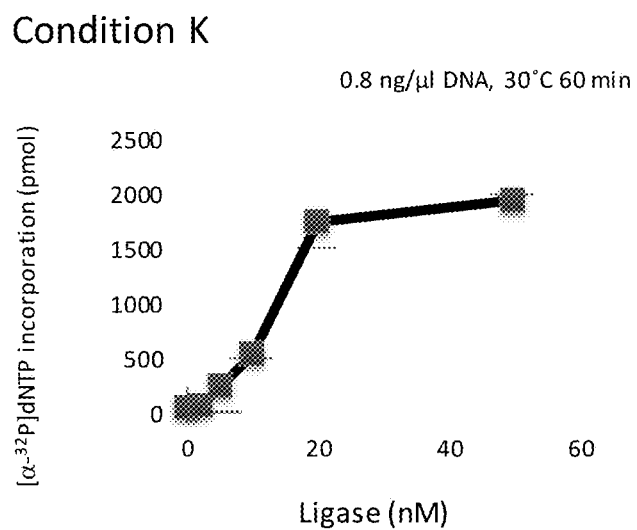
FIG. 21 is a graph showing the results of Condition K (studies regarding the amount of an enzyme having DNA ligase activity) in Example 7.

The results are shown in FIG. 21.

(12) Condition L

The amount of a single-strand DNA binding protein (SSB) in the reaction composition was studied. The concentration of SSB at the initiation of the reaction was set at 0 nM, 10 nM, 20 nM, 50 nM, 100 nM, 200 nM, and 500 nM.

Figure 22:
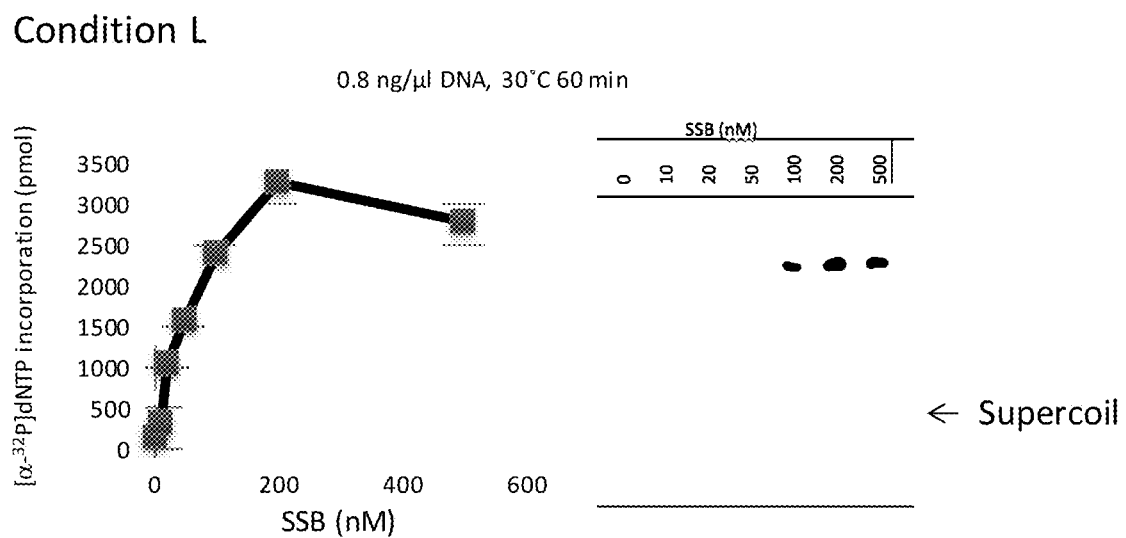
FIG. 22 includes a graph showing the results of Condition L (studies regarding the amount of SSB) and a gel electrophoretic photograph in Example 7.

The results are shown in FIG. 22.

(13) Condition M

The amount of an enzyme having DNA polymerase I activity in the reaction composition was studied. The concentration of Pol I at the initiation of the reaction was set at 0 nM, 2 nM, 5 nM, 10 nM, 20 nM, and 50 nM.

Figure 23:
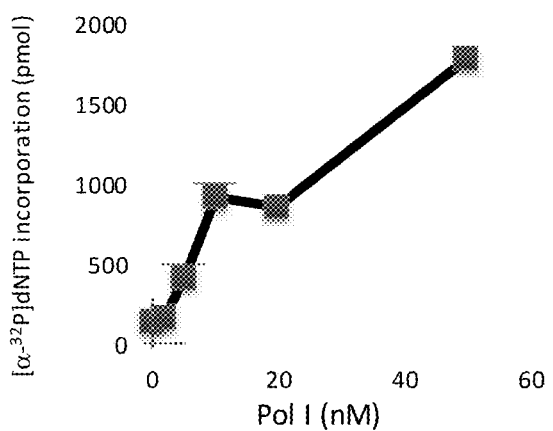
FIG. 23 is a graph showing the results of Condition M (studies regarding the amount of an enzyme having DNA polymerase I activity) in Example 7.

The results are shown in FIG. 23.

(14) Condition N

The amounts of an enzyme having DnaB-type helicase activity and an enzyme having DNA helicase loader activity in the reaction composition were studied. The concentration of a DnaB-DnaC complex at the initiation of the reaction was set at 0 nM, 5 nM, 10 nM, 20 nM, and 40 nM.

Figure 24:
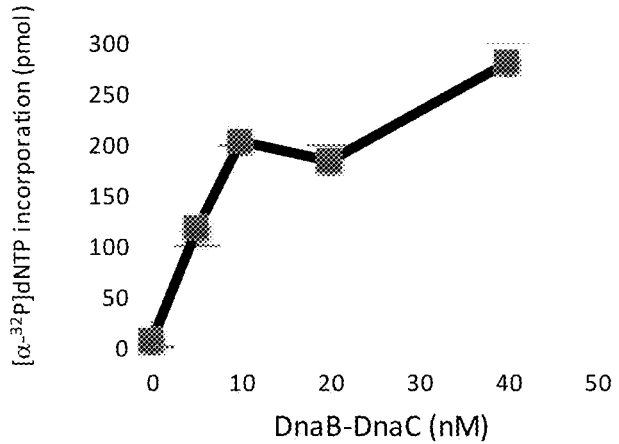
FIG. 24 is a graph showing the results of Condition N (studies regarding the amounts of an enzyme having DnaB-type helicase activity and an enzyme having DNA helicase loader activity) in Example 7.

The results are shown in FIG. 24.

(15) Condition O

The amount of an enzyme having RNaseH activity in the reaction composition was studied. The concentration of RNaseH at the initiation of the reaction was set at 1 nM, 3 nM, and 10 nM.

Figure 25:
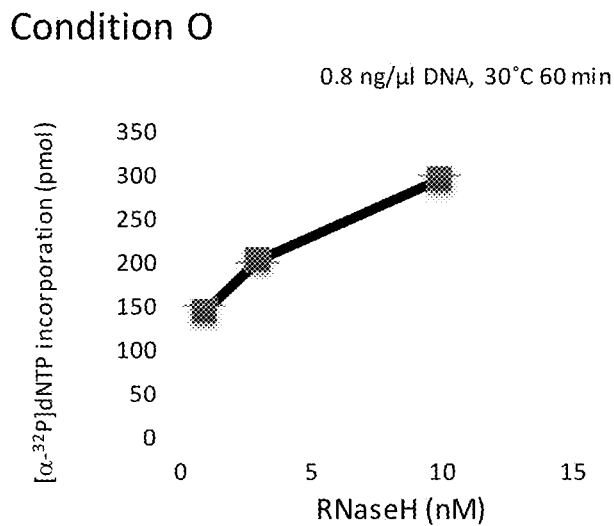
FIG. 25 is a graph showing the results of Condition O (studies regarding the amount of an enzyme having RNaseH activity) in Example 7.

The results are shown in FIG. 25.

(16) Condition P

Regarding Condition P, the amount of template DNA at the initiation of the reaction was set at 8 ng/µl, 0.8 ng/µl, and 0.27 ng/µl, and an amplification reaction was studied.

Figure 26:
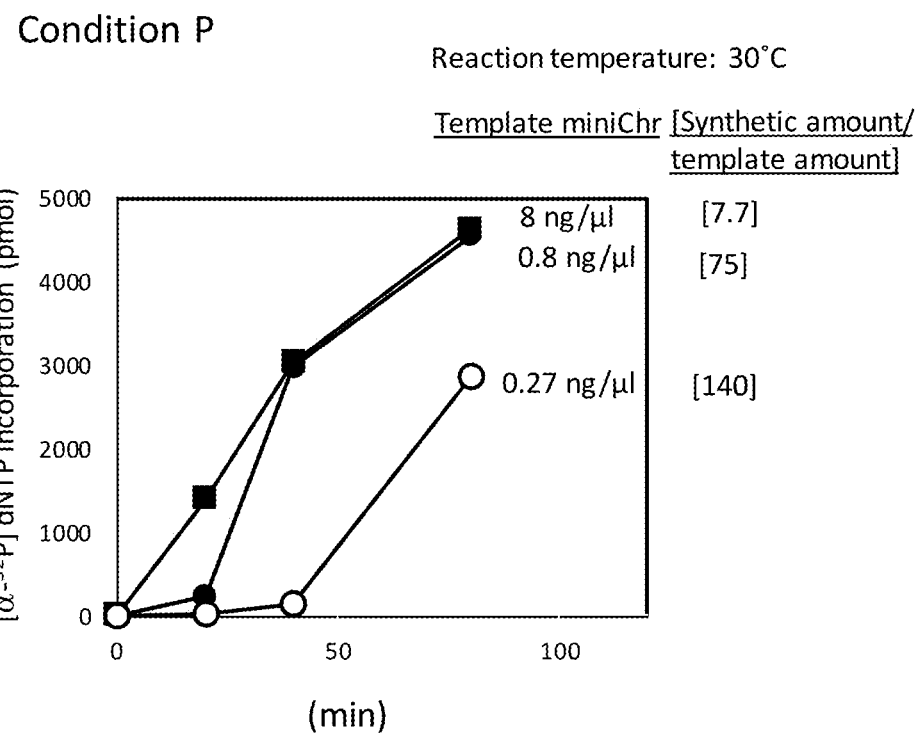
FIG. 26 is a graph showing the results of Condition P in Example 7.

The results are shown in FIG. 26. Under Condition P, even in a case where the amount of template DNA was 0.8 ng/µl, amplification could be efficiently carried out. Further, even in a case where the amount of template DNA was reduced to 0.27 ng/µl, amplification could be efficiently carried out. It could be confirmed that the template DNA was amplified 100 times or more, relative to the amount of DNA synthesized.

(17) Condition Q

Enzymes belonging to the third enzyme group were studied in terms of their amount and composition in the reaction composition. As the third enzyme group, Topo IV, Topo III and RecQ were used. The concentrations studied for individual enzymes are as shown in FIG. 27.

Figure 27:
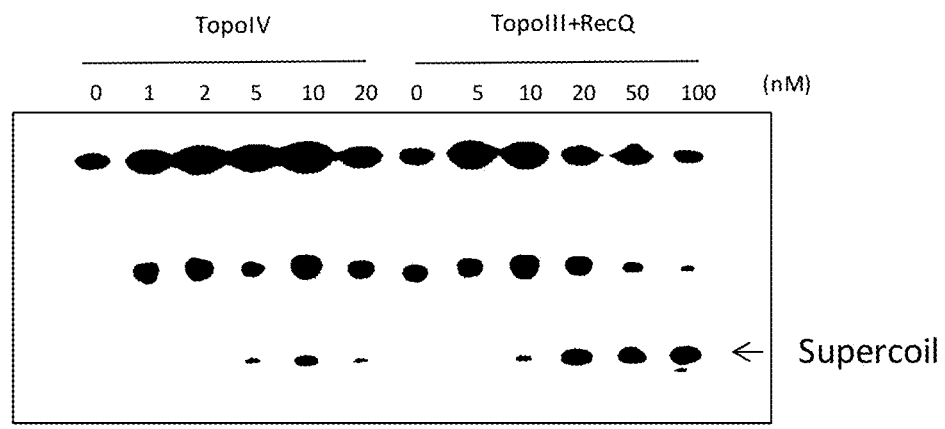
FIG. 27 includes a gel electrophoretic photograph and graphs, showing the results of Condition Q (studies regarding the compositions and amounts of enzymes belonging to the third enzyme group) in Example 7.
Figure 27:
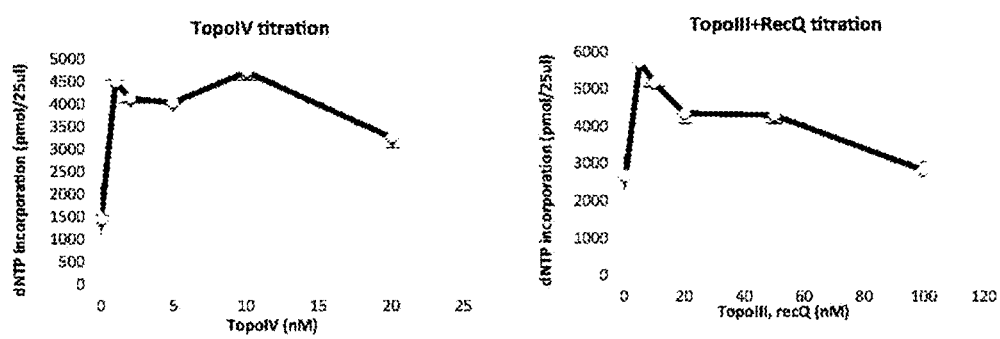
Figure 27:
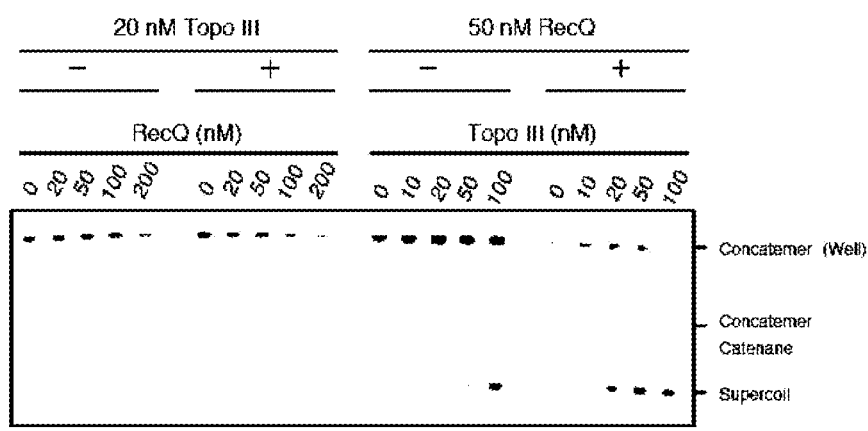

The results are shown in FIG. 27.

(18) Condition R

Regarding Condition R, the amount of DNA gyrase was studied. The concentration of a GyrA-GyrB complex at the initiation of the reaction was set at 0 nM, 10 nM, 25 nM, 50 nM, and 150 nM.

Figure 28:
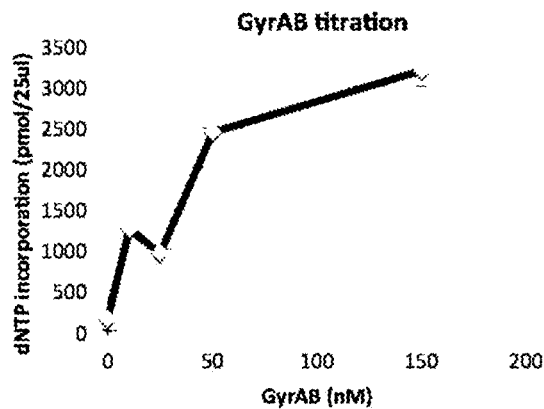
FIG. 28 is a graph showing the results of Condition R in Example 7.

The results are shown in FIG. 28.

(19) Condition S

As Condition S, the concentrations of tRNA, NAD, ammonium sulfate (AS), IHF, SSB, and TopoIV were changed, and thereafter, amplification of circular DNA was studied. The concentrations studied for individual components are as shown in FIG. 29.

Figure 29:
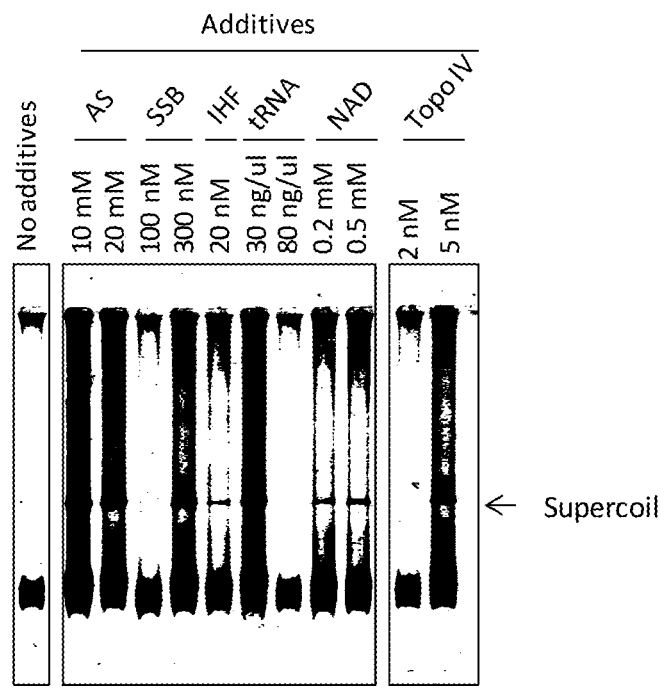
FIG. 29 is a graph showing the results of Condition S in Example 7.

The results are shown in FIG. 29.

Example 8: Modification of Buffer Composition

Conditions for the composition of the reaction buffer shown in Table 1 were further studied.

Specifically, an amplification reaction was carried out in the same manner as that of Example 1, with the exceptions that the 200 kb circular DNA described in Example 1 was used in a concentration of 0.5 pM, and that the composition of the reaction buffer was changed.

(1) Modification of Amount of Dithiothreitol (DTT)

The concentration of DTT, which had been set at 8 mM in Example 1, was changed to 4 mM, and an amplification reaction was then carried out. As a result, it was confirmed that the amplification reaction of circular DNA progressed, although the amount of DTT was reduced to half.

(2) Studies of Alkali Metal Ion Source

Regarding the composition of the reaction buffer in Table 1, the concentration of DTT was changed to 4 mM, and at the same time, a reaction buffer containing no alkali metal ion sources, and a reaction buffer containing, as an alkali metal ion source, 150 mM potassium acetate instead of potassium glutamate, were used. Thereafter, the amplification reaction of circular DNA was carried out.

Figure 30:
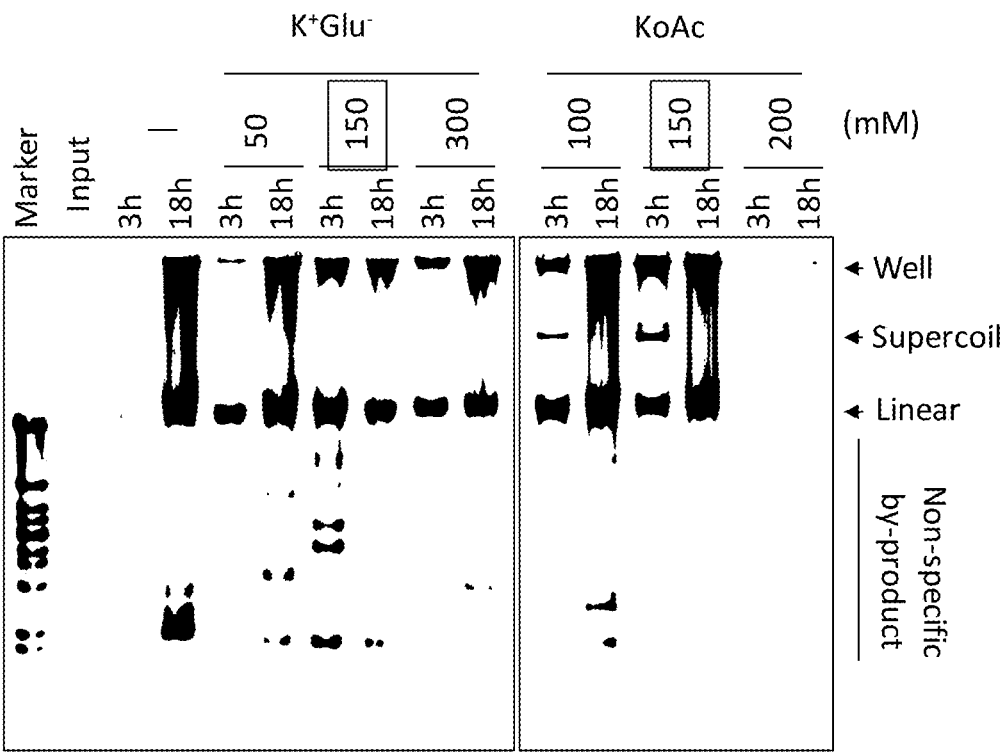
FIG. 30 is a gel electrophoretic photograph showing the results obtained by studying the effect of addition of an alkali metal ion source.

The results are shown in FIG. 30. Amplification of long-chain circular DNA having a low concentration of 0.5 pM or less is problematic in that a low-molecular-weight by-product is amplified, and thus in that generation of a supercoil as an amplification product of interest cannot be confirmed. However, by adding an alkali metal ion source such as potassium glutamate or potassium acetate to a reaction buffer, even in a case where long-chain circular DNA with a low concentration of 0.5 pM was amplified, favorable amplification of a supercoil as a product of interest could be confirmed.

A reaction buffer having the following composition was used in the subsequent experiments.

TABLE 6

| Reaction buffer | |
|---|---|
| Tris-HCl (pH 8.0) | 20 mM |
| Dithiothreitol | 4 mM |
| Potassium acetate | 150 mM |
| Mg(OAc)$_2$ | 10 mM |
| Creatine phosphate | 4 mM |
| rNTPs | 1 mM each |
| NAD | 0.25 mM |
| Ammonium sulfate | 10 mM |
| tRNA | 50 ng/μL |
| dNTPs | 0.1 mM each |
| Bovine serum albumin (BSA) | 0.5 mg/ml |
| Creatine kinase | 20 ng/μL |

(3) Studies of Buffer

With regard to the composition of the buffer shown in Table 6, 20 mM Tris-HCL (pH 8.0) was changed to 20 mM Tris-OAc (pH 8.0), and thereafter, the amplification reaction of circular DNA was carried out. As a result, even in the case of using 20 mM Tris-OAc (pH 8.0), an amplification product was observed at the same level as that in the case of using 20 mM Tris-HCL (pH 8.0).

(4) Studies of Alternatives for Dithiothreitol (DTT)

With regard to the composition of the buffer shown in Table 6, 4 mM DTT was changed to 4 mM 2-mercaptoethanol (2-Me) or 4 mM tris(2-carboxyethyl)phosphine (TCEP), and thereafter, the amplification reaction of circular DNA was carried out. As a result, in either case of using 2-Me or TCEP, an amplification product was observed at the same level as that in the case of using DTT.

(5) Studies of Alternatives for Ammonium Sulfate

With regard to the composition of the buffer shown in Table 6, 10 mM ammonium sulfate was changed to 10 mM ammonium acetate, and thereafter, the amplification reaction of circular DNA was carried out. As a result, even in the case of using ammonium acetate, an amplification product was observed at the same level as that in the case of using ammonium sulfate.

Example 9: Amplification Efficiency Provided by Pre-Incubation of Reaction Solution Effects, which are obtained by performing pre-incubation before the amplification reaction, were studied.

As template DNA, the 200 kb circular DNA described in Example 1 was used. A reaction solution comprising the reaction buffer with the composition shown in Table 6 and the enzyme group with the composition shown in Table 1 was prepared on ice. Pre-incubation was carried out at 0° C., 16° C., or 30° C., for 0, 5, 15 or 30 minutes. Thereafter, the template DNA was added to the reaction solution to a final concentration of 0.05 pM, and the obtained mixture was then the temperature was retained at 30° C. in an incubator for 3 hours. After completion of the reaction, the reaction product was subjected to agarose gel electrophoresis in the same manner as that of Example 1, so that DNA was detected.

Figure 31:
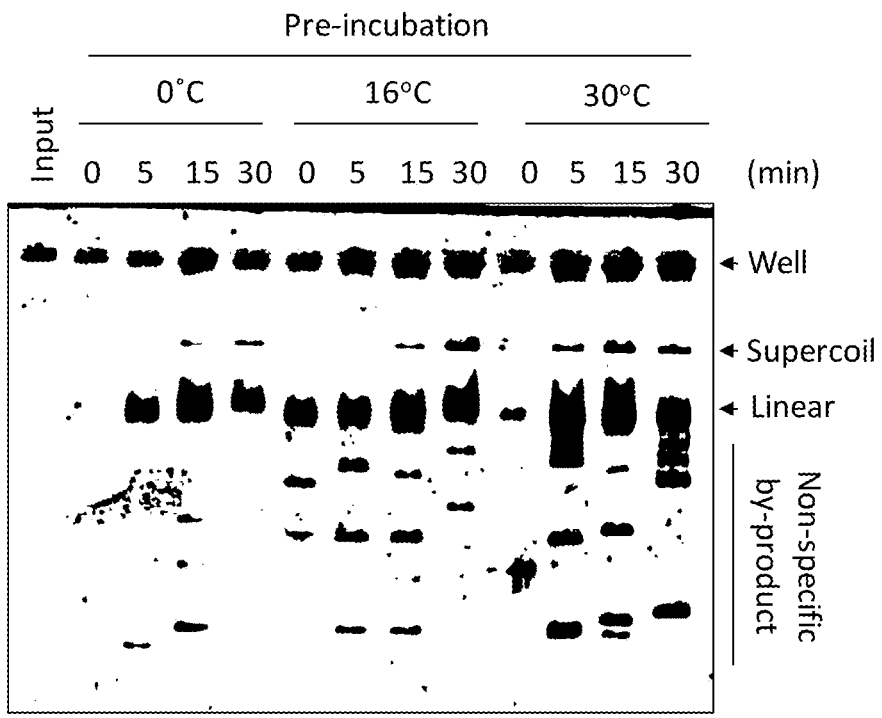
FIG. 31 is a gel electrophoretic photograph showing the results obtained by studying the efficiency of an amplification reaction by pre-incubation.

The results are shown in FIG. 31. It was confirmed that when the pre-incubation was carried out at 16° C. or 30° C., generation of a supercoil as a product of interest was increased. The pre-incubation performed before the amplification reaction is advantageous in that generation of a supercoil as an amplification product of interest is increased even when long-chain circular DNA having a low concentration is amplified.

Example 10: Addition of RecG and RecJ

RecG-type helicase and single-strand DNA-specific exonuclease were further added to the amplification reaction solution, and the effect of the addition of RecG and RecJ to the amplification reaction was studied.

As template DNA, the 200 kb circular DNA described in Example 1 was used.

As RecG-type helicase, RecG was used. RecG was prepared in the same manner as that of Example 6, and was used.

As single-strand DNA-specific exonuclease, RecJ was used. Such RecJ was obtained from NEB.

To a reaction solution comprising the reaction buffer with the composition shown in Table 6 and the enzyme group with the composition shown in Table 1, the 200 kb circular DNA, RecG, and RecJ were added to result in concentrations of 0.5 pM (67 μg/μl), 0 nM or 100 nM, and 0 U/μl or 0.5 U/μl, respectively. The temperature of the obtained amplification reaction solution (10 μl) was retained at 30° C. for 3 hours or 25 hours, so as to carry out an amplification reaction. After completion of the reaction, the reaction product was subjected to agarose gel electrophoresis in the same manner as that of Example 1, so that DNA was detected.

Figure 32:
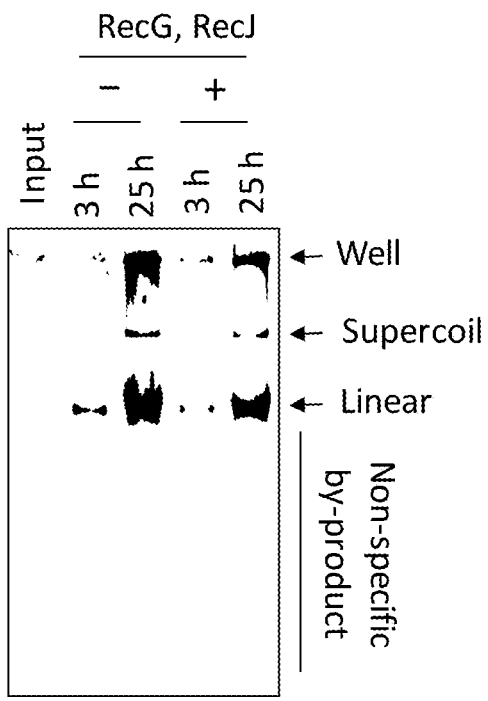
FIG. 32 is a gel electrophoretic photograph showing the results of detection of amplification products in the case of addition of RecG and RecJ.

The results are shown in FIG. 32. By addition of RecG and RecJ, purification of a low-molecular-weight amplification product was reduced, and the improvement of the generated amount of a circular DNA amplification product having a supercoiled structure of interest was observed. In particular, when long-chain circular DNA having a low concentration is amplified, addition of RecG-type helicase and single-strand DNA-specific exonuclease to the amplification reaction is effective as a means for solving the problem that is amplification of a low-molecular-weight by-product.

Example 11: Addition of RecBCD and Exo I

Linear DNA-specific exonuclease and single-strand DNA-specific exonuclease were further added to the amplification reaction solution, and the effects obtained by the addition of the linear DNA-specific exonuclease and the single-strand DNA-specific exonuclease were studied.

As template DNA, the 200 kb circular DNA described in Example 1 was used.

As linear DNA-specific exonuclease, RecBCD was used. Such RecBCD was obtained from NEB.

As single-strand DNA-specific exonuclease, exo I was used. Such exo I was obtained from NEB.

To a reaction solution comprising the reaction buffer with the composition shown in Table 6 and the enzyme group with the composition shown in Table 1, the 200 kb circular DNA, RecBCD, and exo I were added to result in concentrations of 0.5 pM (67 µg/µl), 0, 1.5, 5.0, 15.0, or 50.0 mU/µl, and 200 mU/µl, respectively. The obtained amplification reaction solution (10 µl) was retained at 30° C. for 20 hours, so as to carry out an amplification reaction. After completion of the reaction, the reaction product was subjected to agarose gel electrophoresis in the same manner as that of Example 1, so that DNA was detected.

Figure 33:
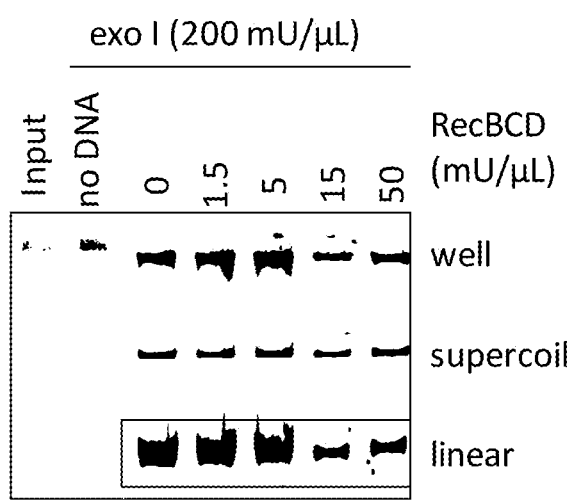
FIG. 33 is a gel electrophoretic photograph showing the results of detection of amplification products in the case of addition of RecBCD and exo I.

The results are shown in FIG. 33. By addition of RecBCD and exo I, generation of linear DNA as a by-product due to the cleavage of DNA, etc. was reduced, and the improvement of the generated amount of a circular DNA amplification product having a supercoiled structure of interest was observed. In particular, when long-chain circular DNA having a low concentration is amplified, addition of linear DNA-specific exonuclease and single strand-specific exonuclease to the amplification reaction is effective as a means for solving the problem that is amplification of linear DNA generated as a by-product.

Example 12: Post-Reaction Treatment—Increase in Final Product by Dilution and Rewarming, and Removal of Linear DNA by RecBCD and Exo I Upon Rewarming Whether or not a by-product can be removed by performing a dilution and rewarming treatment after completion of the amplification reaction was studied. Further, whether or not a by-product can be removed by treating a reaction product with linear DNA-specific exonuclease and/or single strand-specific exonuclease, after completion of the amplification reaction, was also studied.

As template DNA, the 200 kb circular DNA described in Example 1 was used.

As linear DNA-specific exonuclease, RecBCD was used, and as single-strand DNA-specific exonuclease, exo I was used. Such RecBCD and exo I were obtained in the same manner as that of Example 10.

To a reaction solution comprising the reaction buffer with the composition shown in Table 6 and the enzyme group with the composition shown in Table 1, the 200 kb circular DNA was added to result in a concentration of 0.5 pM (67 µg/µl). The temperature of the obtained amplification reaction solution (10 µl) was retained at 30° C. for 23 hours, so as to carry out an amplification reaction.

The reaction solution obtained after completion of the amplification reaction was diluted to 1/5 with a reaction buffer with the composition of Example 6, from which creatine kinase and bovine serum albumin were excluded, and thereafter, (i) the diluted solution was directly rewarmed at 30° C. for 1 hour, (ii) 200 mU/µl RecBCD was added to the diluted solution, and the obtained mixture was then rewarmed at 30° C. for 1 hour, or (iii) 200 mU/µl RecBCD and 200 mU/µl exo I were added to the diluted solution, and the obtained mixture was then rewarmed at 30° C. for 1 hour. Thereafter, the reaction product, together with the product before the dilution and the rewarming, was subjected to agarose gel electrophoresis in the same manner as that of Example 1, so that DNA was detected.

Figure 34:
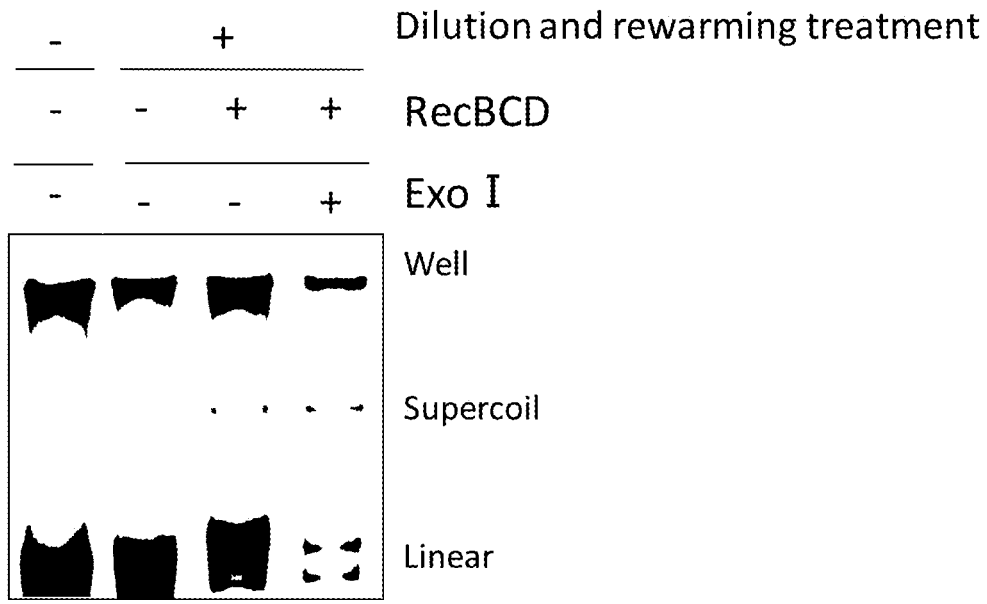
FIG. 34 is a gel electrophoretic photograph showing the results of detection of amplification products in the case of treating reaction products with RecBCD and exo I after completion of an amplification reaction.

The results are shown in FIG. 34. Circular DNA having a supercoiled structure of interest could be detected only by dilution and rewarming of the reaction solution obtained after completion of the amplification reaction. Furthermore, linear DNA as a by-product could be removed in the presence of linear DNA-specific exonuclease and/or single strand-specific exonuclease.

The dilution and rewarming treatment is effective as a means for promoting replication and elongation of an amplified intermediate in the product or a separation reaction thereof, and enhancing the amount of a final product generated as supercoiled DNA.

Further, the treatment of the reaction product with linear DNA-specific exonuclease and single strand-specific exonuclease upon rewarming is effective as a means for removing linear DNA generated as a by-product, in particular, when long-chain circular DNA having a low concentration is amplified.

Example 13: Post-Reaction Treatment—Repair of Single-Strand Gap with Gap Repair (GR) Enzyme Whether or not circular DNA having a supercoiled structure of interest can be detected by treating it with a gap repair (GR) enzyme, after completion of the amplification reaction, was studied.

To a reaction solution comprising the reaction buffer with the composition shown in Table 6 and the enzyme group with the composition shown in Table 1, 15 kb circular DNA was added to result in a concentration of 0.5 pM (5 µg/µl). The temperature of the obtained amplification reaction solution (10 µl) was retained at 30° C. for 20 hours, so as to carry out an amplification reaction. The 15 kb circular DNA used as template DNA was prepared by connecting and cyclizing a 15-kb region on the genome of *Escherichia coli* with an oriC fragment (0.4 kb), then cloning the obtained product using *Escherichia coli*, and then purifying it.

The product obtained after completion of the amplification reaction was dialyzed with 20 ml of 10 mM Tris-HCl (pH 8.0) for 2 hours, and 0.5 µl of the resulting solution was then added to 5 µl of a reaction buffer containing a GR enzyme, followed by performing incubation at 30° C. for 20 minutes or 60 minutes. A combination of Exo III, DNA polymerase I, ligase and gyrase was used as a GR enzyme, and these enzymes were added in concentrations of 20 mU/μl, 50 nM, 50 nM, and 50 nM, respectively. As a reaction buffer, a buffer having the composition shown in Table 6 was used.

As a positive control for the treatment with the GR enzyme, PhiX174 RFII (NEB) that was DNA comprising a nick was used, and a gap repair reaction was carried out. When gap repair is appropriately carried out, the nick is repaired, and circular DNA having a supercoiled structure could be detected.

The reaction product was subjected to agarose gel electrophoresis in the same manner as that of Example 1, so that DNA was detected.

Figure 35:
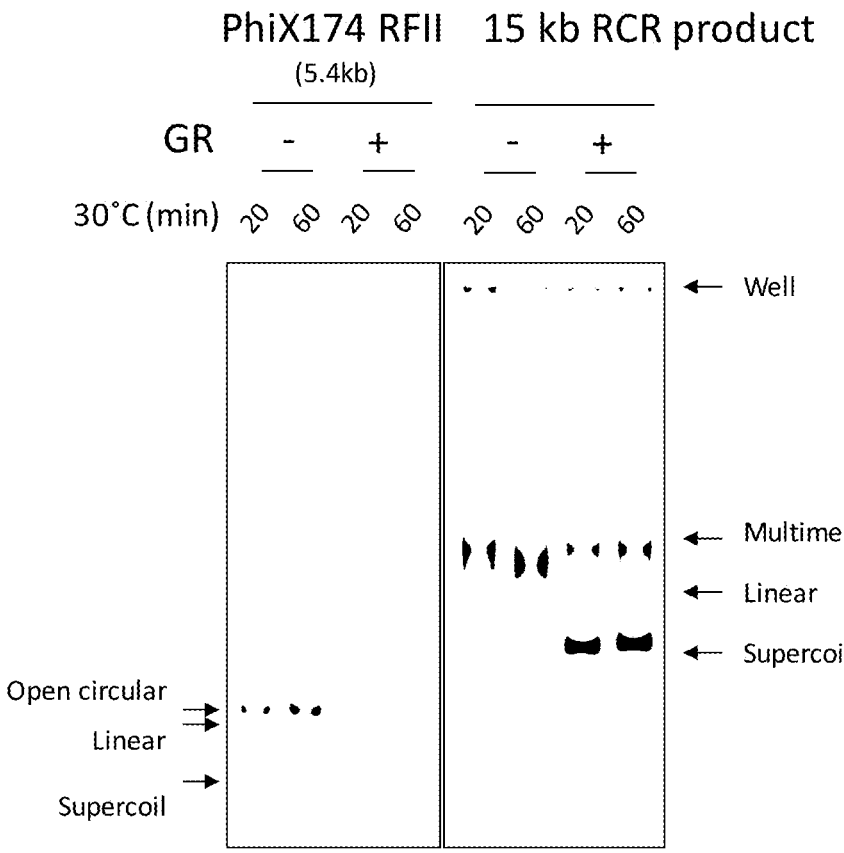
FIG. 35 is a gel electrophoretic photograph showing the results of amplification products in the case of treating reaction products with a gap repair enzyme after completion of an amplification reaction.

The results are shown in FIG. 35. In the present experiment, since the reaction was carried out for a long period of time, which exceeded the optimal amplification time for 15 kb circular DNA (approximately 3 hours), almost no supercoiled products could be observed. Circular DNA having a supercoiled structure could be detected by treating this product with the GR enzyme. These results demonstrate that circular DNA having a supercoiled structure of interest can be obtained by performing gap repair on the by-product generated after the amplification reaction.

Example 14: Long-Chain Circular DNA Stabilizing Factor, and Promotion of Efficient Amplification Reaction Using Same (1) Studies of Long-Chain DNA Stabilizing Factor When long-chain circular DNA was incubated at 37° C. using a reaction buffer with the composition of Example 6, from which creatine kinase and bovine serum albumin were excluded, DNA damage was induced, and a reduction in circular DNA having a supercoiled structure was observed. A reagent contributing to stabilization of long-chain circular DNA was studied.

As a result of the studies, it became clear that glucose, sucrose, dimethyl sulfoxide (DMSO), bovine serum albumin (BSA), ethylene glycol tetraacetic acid (EGTA), bathocuproin disulfonic acid disodium (BDA), penicillamine, Tiron (1,2-dihydroxybenzene-3,5-sulfonate), diethylenetriamine pentaacetic acid (DTPA), ethylenediamine tetraacetic acid (EDTA), a Dps protein, (derived from *Escherichia coli*), and a metallothionein protein (derived from human) exhibit effects on stabilization of DNA, during retention of temperature using the reaction buffer.

(2) Promotion of Efficient Circular DNA Amplification Reaction Using DNA Stabilizing Factor To a reaction solution comprising the reaction buffer with the composition shown in Table 6 and the enzyme group with the composition shown in Table 1, the 200 kb circular DNA, DTPA or Tiron, BDA, and Dps were added to result in concentrations of 0.5 pM (67 μg/μl) (circular DNA), 0.05, 0.1 or 0.3 mM (DTPA or Tiron), 0.1, 0.3 or 1 mM (BDA), and 0.3, 1 or 3 μM (Dps). The temperature of the thus prepared amplification reaction solution (10 μl) was retained at 30° C. for 20 hours, so as to carry out an amplification reaction. The reaction solution obtained after completion of the amplification was diluted and rewarmed at 30° C. for 1 hour in the same manner as that of Example 11, and the reaction product was then subjected to agarose gel electrophoresis in the same manner as that of Example 1, so that DNA was detected.

Figure 36:
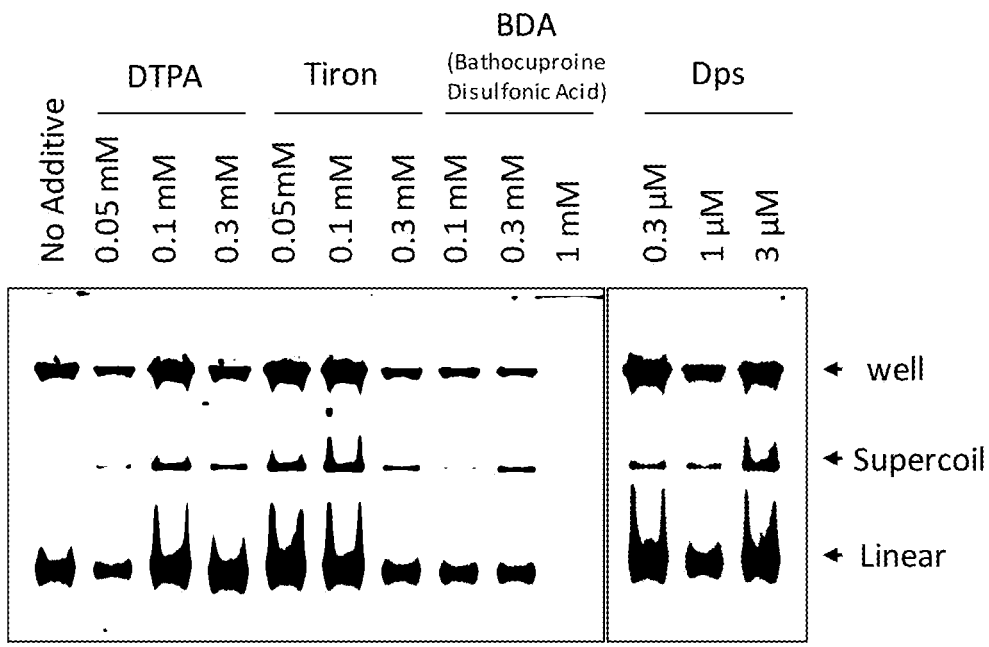
FIG. 36 is a gel electrophoretic photograph showing the results obtained by studying the efficiency of an amplification reaction in the case of using a long-chain circular DNA stabilizing factor.

The results are shown in FIG. 36. It became clear that, in the amplification reaction products, to which DTPA, Tiron, BDA, a Dps protein and BSA had been added among the DNA stabilizing factors found in the above (1), the generated amount of circular DNA having a supercoiled structure was improved, and thus that these DNA stabilizing factors have action to promote an efficient circular DNA amplification reaction.

Example 15: Amplification Reaction of Long-Chain Circular DNA Using Emulsion

The amplification reaction of circular DNA performed in a water-in-oil emulsion was studied.

As template DNA, the 200 kb circular DNA described in Example 1 was used.

To a reaction solution comprising the reaction buffer with the composition shown in Table 6 and the enzyme group with the composition shown in Table 1, the 200 kb circular DNA was added to result in a concentration of 0.5 pM (67 μg/μl), so as to prepare an amplification reaction solution (5 μl). To the prepared amplification reaction solution, 100 μl of mineral oil containing a surfactant (2% ABIL EM90 and 0.05% Triton-X100) was added, and the obtained mixture was then blended by subjecting it to Vortex for 60 seconds. The temperature of the thus obtained mixture was retained at 30° C. for 3 hours or 18 hours, so as to carry out an amplification reaction (emulsion). On the other hand, as a control, the above described amplification reaction solution was directly incubated at 30° C. for 3 hours or 18 hours, so as to carry out an amplification reaction (bulk). Thereafter, the reaction product was subjected to agarose gel electrophoresis in the same manner as that of Example 1, so that DNA was detected.

Figure 37:
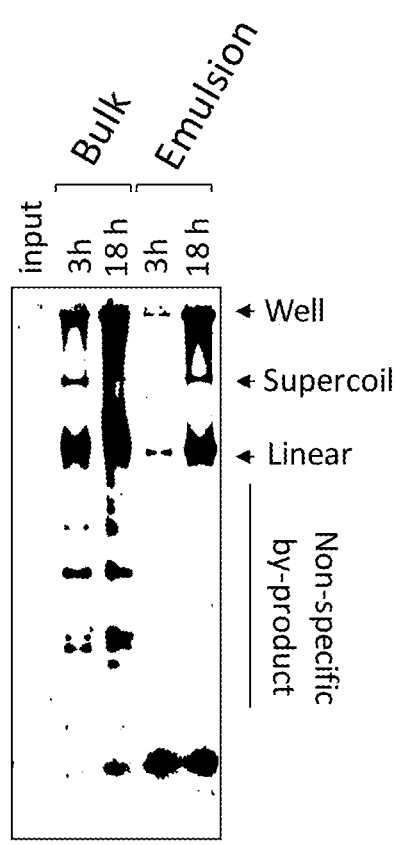
FIG. 37 is a gel electrophoretic photograph showing the results obtained by studying a reaction of amplifying circular DNA in a water-in-oil emulsion.

The results are shown in FIG. 37. In the bulk system, generation of a low-molecular-weight by-product was observed, and when the reaction time was prolonged, DNA having a supercoiled structure of interest was not observed. In the emulsion system, generation of a low-molecular-weight by-product was suppressed, and when the reaction time was prolonged, generation of DNA having a supercoiled structure of interest was improved.

Example 16: Promotion of Efficient Amplification by Temperature Cycle

Since replication of circular DNA is completed promptly in the amplification reaction of the circular DNA, as the molecular weight of the circular DNA is decreased. Thus, if low-molecular-weight circular DNA is generated as a by-product, the by-product is amplified faster than the circular DNA as a target. Amplification of long-chain DNA has been problematic in that the amplification of a by-product becomes superior to the amplification of the long-chain DNA according to this phenomenon, and thus, in that the amplification of the long-chain DNA as a product of interest is suspended. In order to efficiently amplify long-chain DNA, it is necessary to suppress over-amplification of low-molecular-weight DNA.

Under such circumstances, the present inventors have focused on the point that the optimal temperature is 30° C. or higher at the time of initiation of replication of circular DNA comprising oriC, but elongation and/or separation reactions progress even at a lower temperature. Thus, the present inventors have attempted to unify the cycle at the initiation of replication by applying a temperature cycle to the amplification reaction of circular DNA, so as to suppress over-amplification of low-molecular-weight DNA.

A reaction solution comprising the reaction buffer with the composition shown in Table 6 and the enzyme group with the composition shown in Table 1 was pre-incubated at 30° C. for 30 minutes in the same manner as that of Example 8, and the 200 kb circular DNA (Example 1) was then added to the reaction mixture to result in a concentration of 0.5 pM (67 μg/μl), so as to prepare an amplification reaction solution (10 μl). A temperature cycle of 37° C., 5 minutes→16° C. or 24° C., 30 minutes was carried out 30 cycles on the prepared amplification reaction solution (2-Step cycles). On the other hand, as a sample used as a control, the temperature of the above described amplification reaction solution was retained at 30° C. for 21 hours. The reaction product was subjected to agarose gel electrophoresis in the same manner as that of Example 1, so that DNA was detected.

Figure 38:
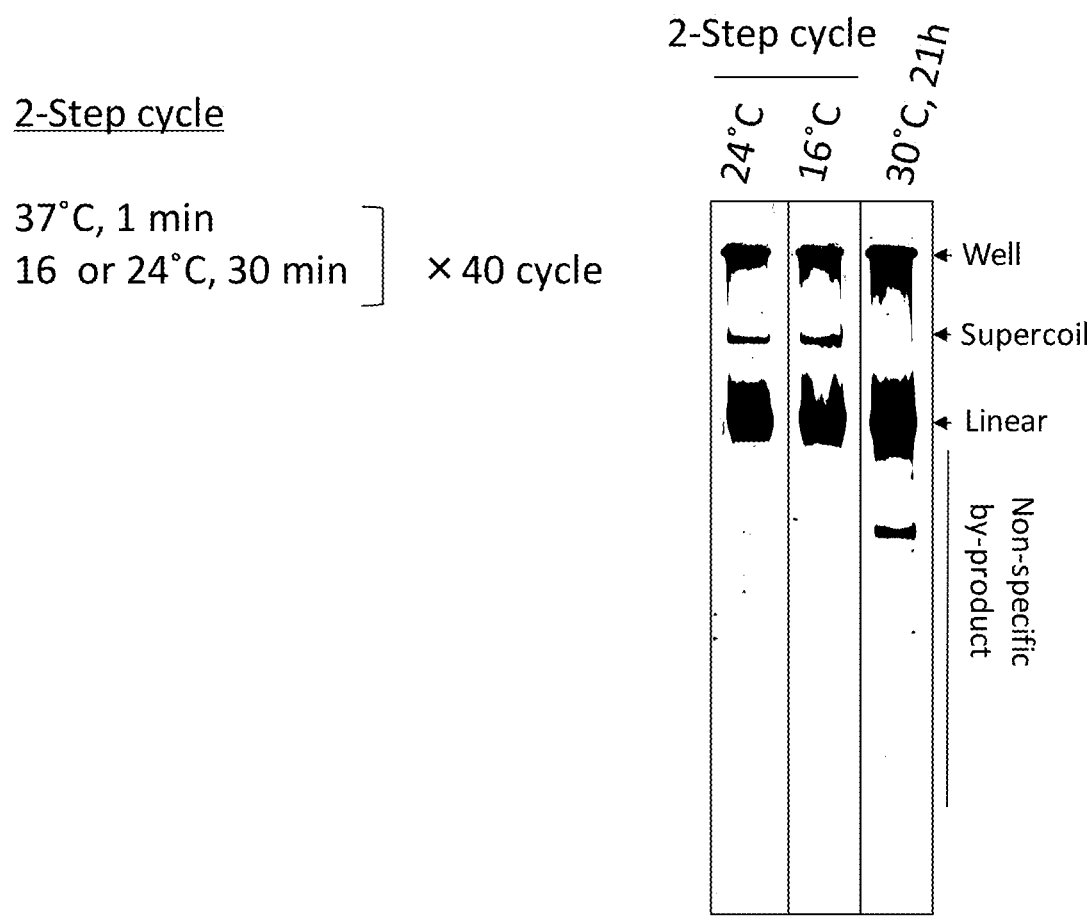
FIG. 38 is gel electrophoretic photograph showing the results of detection of amplification products obtained from an amplification reaction of circular DNA, which involves a temperature cycle.

The results are shown in FIG. 38. In the case of performing the reaction by the 2-Step cycles, generation of a low-molecular-weight by-product was suppressed, and at the same time, the generated amount of DNA having a supercoiled structure of interest was increased.

INDUSTRIAL APPLICABILITY

According to the present invention, there can be provided a method capable of simply and exponentially amplifying circular DNA, and particularly, long-chain circular DNA, without using *Escherichia coli* cells or plasmid vectors.

The invention claimed is:

1. A method for amplifying circular DNA, comprising:
   (1) providing a reaction mixture of circular DNA as a template with a reaction solution comprising:
   a first enzyme group that catalyzes replication of circular DNA, wherein the first enzyme group comprises an enzyme having DnaA activity, one or more types of a nucleoid protein, an enzyme or enzyme group having DNA gyrase activity, single-strand binding protein (SSB), an enzyme having DnaB-type helicase activity, an enzyme having DNA helicase loader activity, an enzyme having DNA primase activity, an enzyme having DNA clamp activity, and an enzyme or enzyme group having *E. coli* DNA Polymerase III* activity;
   a second enzyme group that catalyzes an Okazaki fragment maturation and synthesizes two sister circular DNAs constituting a catenane, wherein the second enzyme group comprises an enzyme having *E. coli* DNA Polymerase I activity and an enzyme having DNA ligase activity;
   a third enzyme group that catalyzes a separation of two sister circular DNAs, wherein the third enzyme group comprises an enzyme having topoisomerase IV activity and/or an enzyme having topoisomerase III activity;
   a buffer;
   ATP;
   GTP, CTP and UTP;
   dNTP;
   a magnesium ion source; and
   an alkali metal ion source,
   wherein the circular DNA includes a replication origin sequence that can bind to an enzyme having DnaA activity; and
   (2) incubating the reaction mixture of (1) in a repeating temperature cycle of an incubation at 30° C. or higher and an incubation at 27° C. or lower.

2. The method according to claim 1, wherein the reaction solution further comprises a protein non-specific adsorption inhibitor and/or a nucleic acid non-specific adsorption inhibitor.

3. The method according to claim 1, wherein the reaction solution further comprises linear DNA-specific exonuclease and/or RecG-type helicase.

4. The method according to claim 1, wherein the reaction solution further comprises an ammonium salt.

5. The method according to claim 1, wherein the reaction solution further comprises an enzyme having RNaseH activity.

6. The method according to claim 1, wherein the reaction solution further comprises an enzyme having RecQ-type helicase activity.

7. The method according to claim 1, wherein
   the one or more nucleoid proteins are IHF or HU,
   the enzyme or the enzyme group having DNA gyrase activity is a complex of GyrA and GyrB,
   the enzyme having DnaB-type helicase activity is DnaB helicase,
   the enzyme having DNA helicase loader activity is DnaC helicase loader,
   the enzyme having DNA primase activity is DnaG primase,
   the enzyme having DNA clamp activity is DnaN clamp, and
   the enzyme group having *E. coli* DNA Polymerase III* is an enzyme group comprising DnaX, HolA, HolB HolC, HolD, DnaE, DnaQ, and HolE.

8. The method according to claim 1, wherein the reaction solution further comprises RecG-type helicase and/or single-strand DNA-specific exonuclease.

9. The method according to claim 1, wherein the reaction solution further comprises linear DNA-specific exonuclease and/or single-strand DNA-specific exonuclease.

10. The method according to claim 1, wherein the reaction solution further comprises a DNA stabilizing factor.

11. The method according to claim 1, wherein
    (1) comprises:
    (1-1) pre-incubating a reaction solution comprising:
    the first enzyme group that catalyzes replication of circular DNA;
    the second enzyme group that catalyzes an Okazaki fragment maturation and synthesizes two sister circular DNAs constituting a catenane;
    the third enzyme group that catalyzes a separation of two sister circular DNAs;
    the buffer;
    ATP;
    GTP, CTP and UTP;
    dNTP;
    the magnesium ion source; and
    the alkali metal ion source; and
    (1-2) forming a reaction mixture of the reaction solution with circular DNA as a template.

12. The method according to claim 1, wherein (2) is carried out in a water-in-oil emulsion.

13. The method according to claim 1, wherein, following (2), the method further comprises:
    (3) performing a post-reaction treatment, comprising:
    (i) diluting the reaction mixture five or more times with the reaction solution that does not contain the first to third enzyme groups, and then rewarming the resultant mixture;
    (ii) treating with linear DNA-specific exonuclease and/or single-strand DNA-specific exonuclease; and/or
    (iii) treating with a gap repair enzyme.

14. The method of claim 1, wherein the replication origin sequence comprises an origin of chromosome (oriC) sequence.

15. The method of claim 1, wherein the enzyme group having *E. coli* DNA Polymerase III* activity comprises DnaX, HolA, HolB, HolC, HolD, DnaE, DnaQ, and HolE.

* * * * *